United States Patent [19]

de Vries et al.

[11] Patent Number: 5,958,707
[45] Date of Patent: *Sep. 28, 1999

[54] HUMAN INTERLEUKIN-4 ANTAGONIST/ AGONIST SCREENS

[75] Inventors: Jan E. de Vries, Los Altos, Calif.; Chung-Her Jenh, Edison, N.J.; Satwant K. Narula, West Caldwell, N.J.; Paul J. Zavodny, Mountainside, N.J.

[73] Assignee: Schering Corporation, Kenilworth, N.J.

[ * ] Notice: This patent is subject to a terminal disclaimer.

[21] Appl. No.: 08/453,024

[22] Filed: May 30, 1995

Related U.S. Application Data

[60] Division of application No. 08/070,162, May 28, 1993, which is a continuation-in-part of application No. 07/869,914, Apr. 16, 1992, abandoned, which is a continuation-in-part of application No. 07/770,081, Oct. 3, 1991, abandoned.

[51] Int. Cl.$^6$ .................................................. G01N 33/53
[52] U.S. Cl. ..................... 435/7.2; 435/69.1; 435/252.3; 435/320.1; 435/325; 935/27; 935/36; 935/55; 935/56
[58] Field of Search ........................... 435/7.1, 7.2, 69.1, 435/252.3, 320.1, 325; 530/350; 935/22, 27, 34, 55, 56, 36

[56] References Cited

FOREIGN PATENT DOCUMENTS

WO 90/10710  9/1990  WIPO .

OTHER PUBLICATIONS

Cato et al. (1986) The EMBO Journal, vol. 5, No. 9, pp. 2237–2240.
Alberts, et al., *Molecular Biology of the Cell*, 2 ed., p. 218, Garland Publishing Inc., (New York, N.Y. 1989).
An, et al., *Mol. Cell. Biol.*, 2, 1628 (1982).
Boothby, et al., *Science*, 242, 1559 (1988).
Defrance, et al., *J. Exp. Med.*, 165, 1459 (1987).
Gauchat, et al., *J. Exp. Med.*, 172, 463 (1990).
Gauchat, et al., *J. Immunol.*, 148, 2291 (1992).
Hall, et al., Biosis Abstract No. 76033467.
Kikutani, et al., *Cell*, 47, 657 (1986).
Maniatis, et al., *Molecular Cloning: A Laboratory Manual*, pp. 73–88, ColdSpring Harbor Laboratory Press (ColdSpring Harbor, N.Y. 1982).
Mills, et al., *Nucleic Acids Res.*, 18, 7305 (1990).
Milman, et al., *Somatic Cell. Genet.*, 7, 161 (1981).
Pene, et al., *Proc. Natl. Acad. Sci., U.S.A.*, 85, 6880 (1988).
Prete, et al., *J. Immunol.*, 140, 4193 (1988).
Rothman, et al., *Mol. Cell. Biol.*, 10, 1672 (1990).
Rothman, et al., *Mol. Cell. Biol.*, 11, 5551 (1991).
Rousset, et al., *J. Immunol.*, 140, 2625 (1988).
Sambrook, et al., "Molecular Cloning: A Laboratory Manual", pp. 16.41–16.46, ColdSpring Harbor Laboratory Press (ColdSpring Harbor, N.Y. 1989).
"SCRIP Biotechnology Made Simple—A Glossary of Recombinant DNA and Hybridoma Technology", 3rd ed., pp. 59–63, PJB Publications Ltd., (Richmond, Surrey, United Kingdom 1987).
Stavnezer, et al., *Proc. Natl. Acad. Sci., U.S.A.*, 85, 7704 (1988).
Suter, et al., *Nucleic Acids Res.*, 15, 7259 (1987).
Suter, et al., *J. Immunol.*, 143, 3087 (1989).
Takai, et al., *Biochim. Biophys. Acta.*, 1048, 105 (1990).
Vercelli, et al., *J. Exp. Med.*, 167, 1406 (1988).
Williams, et al., *Analytical Biochem.*, 176,28 (1989).
Hall, et al., *J. Mol. Appl. Gen.*, 2, 101–110 (1983).
Xu, *Proc. Natl. Acad. Sci., U.S.A.*, 90, 3705–3709 (1993).
Jabara, et al., *J. Immunol.*, 145, 3468–3473 (1990).
Qiu, et al., *Eu. J. Immunol.*, 20, 2191–2199 (1990).
Sambrook, et al., "Molecular Cloning: A Laboratory Manual", excerpts from Ch. 16, incl., 16.57, ColdSpring Harbor Laboratory Press (ColdSpring Harbor, N.Y. 1989).
Wurm, *Biologicals*, 18, 159–164 (1990).

*Primary Examiner*—John Ulm
*Assistant Examiner*—Prema Mertz
*Attorney, Agent, or Firm*—Norman C. Dulak; Immac J. Thampoe

[57] ABSTRACT

Stably-transformed human cell lines containing a reporter gene operatively linked to an IL-4-responsive element are provided. In some embodiments a human Fc$_\epsilon$RII IL-4-responsive element is used. In other embodiments a human germline $\epsilon$ transcript promoter is used as the responsive element. Also provided are methods for using such transformed cell lines to screen for agonists and/or antagonists of human interleukin-4.

18 Claims, 10 Drawing Sheets

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 1127 base pairs
      (B) TYPE: nucleic acid
      (C) STRANDEDNESS: double
      (D) TOPOLOGY: linear (xi) SEQUENCE DESCRIPTION: SEQ ID NO: 1:

```
GTATCTTTCT TTCCCCCGCT TCCCTCCTTC CCTCCTACTC CTCCTTCTCC        50

CTCTCCTTCC TTCTGTCTTT TTTTTCCCCT TCCTCTGCCT CTCTCTCCTC       100

TTCCCTTTTT TCTTGCTGGG ACTCAAACCT GGGACATTTG ACCTGGGAGC       150

CTATTTGCTC AATCATCAAG AGACATAATC TCATGGTGGG GTGTCTGCTG       200

GTAAGTGCCG GGTGGCAGGA TCCCAACTCC AGGCCGTCCT TCTAACCCAA       250

GAGGCCCTGC CTCTGCCTAG AGCCTTCCGT GGCTCCCCAG GGCCCTCTGT       300

GATCGGCCAT AGTGGTATGA TTCAGTGTGC AGTAACAGTG GTTCACATCT       350

TGACGCTACC ACTCACCTCC TTCAGCCCTG TGGGAACTTG CTGCTTAACA       400

TCTCTAGTTC TCACCCAATT CTCTTACCTG AGAAATGGAG ATAATAATAA       450

CACGGACTTC ACCGGGTGTG GGGAGCACCA GGAGAGGCCA TGCGTGTAAT       500

GTTATCCGGG TGGCAAGCCC ATATTTAGGT CTATGAAAAT AGAAGCTGTC       550
```

```
AGTGGCTCTA CTTTCAGAAG AAAGTGTCTC TCTTCCTGCT TAAACCTCTG         600

TCTCTGACGG TCCCTGCCAA TCGCTCTGGT CGACCCCAAC ACACTAGGAG         650

GACAGACACA GGCTCCAAAC TCCACTAAGT GAGTACGTAT CTGGTGTGTT         700

GGGGGTTGGC CCATGGGCAG TGGAGATCAA AGCGCCCTTG GAAGAAACGA         750

CCTTGGGCTG AGCCTCAAGG GATGACCAGC AGGAGGTCAC AACCAGAGAA         800

GGGAGGTGGT GGGTGGTGAG GGGGCGGGGG TGGGGCCGC AGTGTGGACA          850

GAATCTCGAG GCATTCGAGT CCCTGATTTG GGGAAGTGAA AGCAGGCCAT         900

CTGGTCTGAG ATGAGCTTGG TGAGTGCGCT GGGCCGATCA TAGAGGGCCC         950

TGGGGAGCCA TGGAAGACTC TAGGCAGAGG CAGGACCTCT TGGGTTAGAA         1000

GGACGGCCTG GAGTTGGGAT CCTGCCACCC AGCACTTACC AGTAGACACC        1050

CCACCATGAG ATTATGTCTC CAGATGATTG AGCAAATGGG CTCCCAGCTC        1100

AAGGGTCCCG GGTTTGAGTT CAGTCCC                                 1127
```

(2) INFORMATION FOR SEQ ID NO: 2:

(i) SEQUENCE CHARACTERISTICS:
        (A) LENGTH:    587 base pairs
        (B) TYPE:    nucleic acid
        (C) STRANDEDNESS:    double
        (D) TOPOLOGY:    linear (xi) SEQUENCE DESCRIPTION: SEQ ID NO: 2:

```
GGATCCCCGG CTGCAGGACA GTGACCTGGG AGTGAGTACA AGGTGAGGCC          50

ACCACTCAGG GTGCCAGCTC CAAGCGGGTC ACAGGGACGA GGGCTGCGGC         100

CATCAGGAGG CCCTGCACAC ACATCTGGGA CACGCGCCCC GAGGGCCAGT         150

TCACCTCAGT GCGCCTCATT CTCCTGCACA AAAGCGCCCC CATCCTTTCT         200

TCACAAGGCT TTCGTGGAAG CAGAGGCGTC GATGCCCAGT ACCCTCTCCC         250

TTTCCCAGGC AACGGGACCC CAAGTTTGCT GACTGGGACC ACCAAGCCAC         300

GCATGCGTCA AGAGTAGAGT CCGGGACCTA GGCAGGGGCC CTGGCGTTGG         350

GCCTGAGAGA GAAGAGAACC TCCCCAGCAC TCGGTGTGCA TCGGTAGTGA         400

ACCAGCCTCA CCTGACCCCC GCTGTTGCTC AATCGACTTC CCAAGAACAG         450

AGAGAAAAGG GAACTTCCAG GGCGGCCCGG GCCTCCTGGG GTTCCCACCC         500

CATTTTTAGC TGAAAGCACT GAGGCAGAGC TCCCCCTACC CAGGCTCCAC         550

TGCCCGGCAC AGAAATAACA ACCACGGTTA CTGATCA                      587
```

(2) INFORMATION FOR SEQ ID NO: 3:

(i) SEQUENCE CHARACTERISTICS:
        (A) LENGTH:    28 base pairs
        (B) TYPE:    nucleic acid
        (C) STRANDEDNESS:    single
        (D) TOPOLOGY:    linear (xi) SEQUENCE DESCRIPTION: SEQ ID NO: 3:

```
TTCCTCGAGT CTAGATGTGA TCGGCCAT                                 28
```

(2) INFORMATION FOR SEQ ID NO: 4:

(i) SEQUENCE CHARACTERISTICS:
        (A) LENGTH:    39 base pairs
        (B) TYPE:    nucleic acid
        (C) STRANDEDNESS:    single (D) TOPOLOGY:    linear (xi) SEQUENCE DESCRIPTION: SEQ ID NO: 4:

TTCTCTAGAA AGCTTGTCGA CCCCGGGATA ACATTACAC                                   39

(2) INFORMATION FOR SEQ ID NO: 5:

(i) SEQUENCE CHARACTERISTICS:
        (A) LENGTH:    38 base pairs
        (B) TYPE:    nucleic acid
        (C) STRANDEDNESS:    single
        (D) TOPOLOGY:    linear (xi) SEQUENCE DESCRIPTION: SEQ ID NO: 5:

TTCGTCGACA AGCTTCAGCT GTGGAATGTG TGTCAGTT                                    38

(2) INFORMATION FOR SEQ ID NO: 6:

(i) SEQUENCE CHARACTERISTICS:
        (A) LENGTH:    32 base pairs
        (B) TYPE:    nucleic acid
        (C) STRANDEDNESS:    single
        (D) TOPOLOGY:    linear (xi) SEQUENCE DESCRIPTION: SEQ ID NO: 6:

TTCGGATCCA AGCTTTTTGC AAAAGCCTAG GC                                          32

(2) INFORMATION FOR SEQ ID NO: 7:

(i) SEQUENCE CHARACTERISTICS:
        (A) LENGTH:    30 base pairs
        (B) TYPE:    nucleic acid
        (C) STRANDEDNESS:    single
        (D) TOPOLOGY:    linear (xi) SEQUENCE DESCRIPTION: SEQ ID NO: 7:

TTCCTCGAGC CGGCTGCAGG ACAGTGACCT                                             30

(2) INFORMATION FOR SEQ ID NO: 8:

(i) SEQUENCE CHARACTERISTICS:
        (A) LENGTH:    29 base pairs
        (B) TYPE:    nucleic acid
        (C) STRANDEDNESS:    single
        (D) TOPOLOGY:    linear (xi) SEQUENCE DESCRIPTION: SEQ ID NO: 8:

TTCAAGCTTT GATCAGTAAC CGTGGTTGT                                              29

(2) INFORMATION FOR SEQ ID NO: 9:

(i) SEQUENCE CHARACTERISTICS:
        (A) LENGTH:    24 base pairs
        (B) TYPE:    nucleic acid
        (C) STRANDEDNESS:    single
        (D) TOPOLOGY:    linear (xi) SEQUENCE DESCRIPTION: SEQ ID NO: 9:

TTCGGATCCC AAGGCCCAAC TCCC                                                   24

(2) INFORMATION FOR SEQ ID NO: 10:

(i) SEQUENCE CHARACTERISTICS:
        (A) LENGTH:    51 base pairs
        (B) TYPE:    nucleic acid
        (C) STRANDEDNESS:    single
        (D) TOPOLOGY:    linear (xi) SEQUENCE DESCRIPTION: SEQ ID NO: 10:

```
TTCGAATTCA GTCAGACAAA ATGATGCAAC TTAATTTTAT TAGGACAAGG          50

C                                                              51
```

HUMAN INTERLEUKIN-4 ANTAGONIST/AGONIST SCREENS

This is a division of U.S. Application Ser. No. 08/070,162, filed May 28, 1993, which in turn is a continuation-in-part of U.S. Application Ser. No. 07/869,914 filed Apr. 16, 1992 now abandoned, which is a continuation-in-part of Ser. No. 07/770,081, filed Oct. 3, 1991, now abandoned.

TECHNICAL FIELD

The present invention relates to stably-transformed human cell lines containing a reporter gene operatively linked to a promoter comprising an interleukin-4-responsive element. Among the responsive elements that can be used are the human $Fc_\epsilon RII$ (CD23) interleukin-4-responsive element and the germline epsilon transcript promoter. This invention also relates to methods for the use of such transformed cell lines to identify agonists and/or antagonists of human interleukin-4.

BACKGROUND OF THE INVENTION

Interleukin-4 (IL-4) is a protein which affects a broad spectrum of hematopoietic cells [Strober et al., Pediatr. Res. 24:549 (1988)]. IL-4 enhances a number of activities including macrophage function, IgG4 and IgE production, and the proliferation of immunoglobulin-stimulated B cells, antigen-stimulated T cells and erythropoietin-stimulated red blood cell progenitors. It also increases the proliferation of IL-3-stimulated mast cells.

Together with IgE, mast cells play a central role in allergic reactions. Mast cells are granule-containing connective tissue cells which are located proximally to capillaries throughout the body, with especially high concentrations in the lungs, skin and gastrointestinal and genitourinary tracts. Following exposure to an antigenic substance, mast cells degranulate and release chemical mediators such as histamine, serotonin, heparin, prostaglandins etc. to produce an allergic reaction.

The $Fc_\epsilon$ receptor II ($Fc_\epsilon RII$) functions in B cell differentiation and in IgE-mediated immunity. It is the low affinity receptor ($10^7$–$10^8$/M) for the Fc portion of IgE and is positioned with its amino terminus in the cytoplasm and its carboxyl terminus outside the cell [Kikutani et al., Cell 47:657 (1986)]. $Fc_\epsilon RII$, also known as CD23 antigen, is a B cell-specific differentiation antigen restricted to mature B cells expressing IgM/IgD. $Fc_\epsilon RII$ is not found on immature bone marrow B cells, suggesting that it might be involved in the regulation of growth or differentiation of B cells.

An important role for $Fc_\epsilon RII$ in allergic reactions and immunity to parasitic infection has also been suggested, because it is present on certain populations of eosinophils and monocytes. Furthermore, interleukin-4 (IL-4), which is known to be responsible for the isotype switching of B cells to IgE, has been shown to induce $Fc_\epsilon RII$ expression on B cells [Defrance et al., J. Exp. Med. 165:1459 (1987)], monocytes [Vercelli et al., J. Exp. Med. 167:1406 (1988)], and Burkitt's lymphoma cell lines [Rousset et al., J. Immunol. 140:2625 (1988)]. The biological significance of CD23 induction on human B cells by IL-4 remains to be determined, but it has been indicated that truncated forms of CD23 can be secreted and can act as an IgE binding factor, which might be involved in the IgE-mediated immunity.

The induction of CD23 surface expression on human B and Burkitt's lymphoma (BL) cell lines by IL-4 is correlated with enhanced transcription of the specific mRNA (Rousset et al., supra). The specific promoter regulatory element for the IL-4 induction of CD23 expression in Jijoye cells (a BL cell line) has been defined by transiently expressing fusion genes with different portions of the CD23 promoter linked to a chloramphenicol acetyl transferase (CAT) reporter gene [Suter et al., J. Immunol. 143:3087 (1989)]. The genomic DNA element responsible for IL-4 induction of CD23 expression was located within the first 250 bp 5' of the transcription initiation start site.

Human IL-4 induction of this DNA element of CD23 linked to a CAT reporter gene in the transient expression system was about 2 fold. To date, this transient study appears to be the only one using a reporter gene for evaluating CD23 regulation by human IL-4. Most of the studies regarding CD23 expression have used indirect immunofluorescence staining of the $Fc_\epsilon RII$ protein.

The effector function of antibody molecules is determined by the constant region of the immunoglobulin (Ig) heavy chain ($C_H$). Antibodies retain their specificity while their effector functions are changed by isotype switching at the DNA level.

In vitro studies using murine B cell lines indicate that Ig class switching is preceded by expression of the corresponding germline $C_H$ gene [Stavnezer et al., Proc. Natl. Acad. Sci. USA 85:7704 (1988)]. In in vitro studies of human B cells also, it has been shown that germline epsilon ($\epsilon$) transcript synthesis precedes and is required for subsequent $\epsilon$ switching and IgE production [Gauchat et al., J. Exp. Med. 172:463 (1990)].

Rothman et al. [Mol. Cell. Biol. 11:5551 (1991)] have shown that induction of germline $\epsilon$ sequence transcription in an Abelson murine leukemia virus-transformed pre-B cell line is under the control of an IL-4-responsive element located at the promoter of germline $\epsilon$ transcripts. IL-4 is one of only two cytokines that are presently known to specifically induce germline $\epsilon$ sequence transcription.

Recent studies have shown that human germline $\epsilon$ RNA comprises, in addition to the C$\epsilon$ exons [Qiu et al., Eur. J. Immunol. 20:2191 (1990)], a germline $\epsilon$ exon located 3.5 kilobases upstream from C$\epsilon$ [Gauchat et al., supra; Jabara et al., J. Immunol. 145:3468 (1990)] and 5' from S$\epsilon$. Synthesis of this RNA in highly purified normal B cells (Gauchat et al., supra; Jabara et al., supra) and in EBV transformed human B cells (Jabara et al., supra) or Burkitt's lymphoma cells can be induced by IL-4.

Because of the stimulatory effects of IL-4 on IgE production and mast cell proliferation, antagonists of IL-4 may be useful for the treatment of allergies by decreasing mast cell growth and IgE production. Increasing evidence suggests, however, that IL-4 may also have beneficial therapeutic applications [see, e.g., Tepper et al., Cell 57:503 (1989)]. There is thus a need to identify both antagonists and agonists of IL-4.

The search for such agonists and antagonists would be facilitated by the availability of fast and effective in vitro screening systems.

SUMMARY OF THE INVENTION

The present invention fills this need by providing materials and methods for such screening.

More particularly, this invention provides human cell lines which have been stably transformed by a recombinant vector comprising a reporter gene operatively linked to a promoter comprising a human $Fc_\epsilon RII$ IL-4-responsive element, which element has a nucleotide sequence defined by a subsequence of the sequence of SEQ ID NO: 1 and is delimited at the 5' end by one of bases 1 to 298 and at the 3' end by one of bases 507 to 678 of the sequence defined by SEQ ID NO: 1.

This invention further provides human cell lines which have been stably transformed by a recombinant vector comprising a reporter gene operatively linked to a human germline ε transcript promoter, and recombinant vectors that can be used to make such stably transformed cell lines.

This invention still further provides methods for detecting human IL-4 agonists in samples comprising:

(a) providing a human cell line which has been stably transformed by a recombinant vector comprising a reporter gene operatively linked to a promoter comprising a human Fc$_ε$RII IL-4-responsive element, which element has a nucleotide sequence defined by a subsequence of the sequence of SEQ ID NO: 1 and is delimited at the 5' end by one of bases 1 to 298 and at the 3' end by one of bases 507 to 678 of the sequence defined by SEQ ID NO: 1;

(b) contacting the transformed cell line with a sample suspected to contain a human IL-4 agonist, under conditions in which human IL-4 would cause increased expression of the reporter gene; and (c) measuring the level of expression of the reporter gene, whereby the presence of a human IL-4 agonist in the sample is detected by measurement of an increased level of expression of the reporter gene, compared to the level produced in the absence of such agonist.

This invention still further provides methods for detecting human IL-4 antagonists in samples comprising:

(a) providing a human cell line which has been stably transformed by a recombinant vector comprising a reporter gene operatively linked to a promoter comprising a human Fc$_ε$RII IL-4-responsive element, which element has a nucleotide sequence defined by a subsequence of the sequence of SEQ ID NO: 1 and is delimited at the 5' end by one of bases 1 to 298 and at the 3' end by one of bases 507 to 678 of the sequence defined by SEQ ID NO: 1;

(b) contacting the transformed cell line with a sample suspected to contain a human IL-4 antagonist, to which has been added an amount of human IL-4 that, absent such antagonist, would produce a measurable increase in expression of the reporter gene; and (c) measuring the level of expression of the reporter gene, whereby the presence of a human IL-4 antagonist in the sample is detected by measurement of a decreased level of expression of the reporter gene, compared to the level produced by the human IL-4 in the absence of such antagonist.

The present invention still further provides methods for detecting human IL-4 agonists in samples comprising:

(a) providing a human cell line which has been stably transformed by a recombinant vector comprising a reporter gene operatively linked to a human germline ε transcript promoter;

(b) contacting the transformed cell line with a sample suspected to contain a human IL-4 agonist, under conditions in which human IL-4 would cause increased expression of the reporter gene; and (c) measuring the level of expression of the reporter gene, whereby the presence of a human IL-4 agonist in the sample is detected by measurement of an increased level of expression of the reporter gene, compared to the level produced in the absence of such agonist.

This invention still further provides methods for detecting human IL-4 antagonists in samples comprising:

(a) providing a human cell line which has been stably transformed by a recombinant vector comprising a reporter gene operatively linked to a human germline ε transcript promoter;

(b) contacting the transformed cell line with a sample suspected to contain a human IL-4 antagonist, to which has been added an amount of human IL-4 that, absent such antagonist, would produce a measurable increase in expression of the reporter gene; and (c) measuring the level of expression of the reporter gene, whereby the presence of a human IL-4 antagonist in the sample is detected by measurement of a decreased level of expression of the reporter gene, compared to the level produced by the human IL-4 in the absence of such antagonist.

Preferably, the germline ε transcript promoter used in the vectors and methods of the invention comprises DNA having a nucleotide sequence defined by the sequence of bases 7 to 587 of SEQ ID NO: 2.

It is also preferred that the methods employing the human germline ε transcript promoter be carried out in the presence of anti-CD40 antibodies, preferably monoclonal antibodies.

BRIEF DESCRIPTION OF THE FIGURES

This invention can be more readily understood by reference to the accompanying Figures, in which.

DESCRIPTION OF THE INVENTION

All references cited herein are hereby incorporated in their entirety by reference. All nucleic acid sequences disclosed follow the normal 5' to 3' convention, as read from left to right. Standard single-letter abbreviations are used for the nucleotide bases in the sequences (37 C.F.R. § 1.822).

As used herein, the term "agonist" is defined as a substance that, like human IL-4, stimulates (induces) expression of a gene operatively linked to a human $Fc_\epsilon RII$ IL-4 responsive element or a human germline ε transcript promoter. The term "antagonist" is defined as a substance that blocks or inhibits such stimulatory activity by IL-4.

A "reporter gene" can be either a DNA molecule isolated from genomic DNA, which may or may not contain introns, or a complementary DNA (cDNA) prepared using messenger RNA as a template. In either case, the DNA encodes an expression product that is readily measurable, e.g., by biological activity assay, enzyme-linked immunosorbent assay (ELISA) or radioimmunoassay (RIA).

The term "$Fc_\epsilon RII$ IL-4 responsive element" is defined herein to mean a part of the 5' region of the human $Fc_\epsilon RII$ gene which, when operatively associated with a promoter, renders the promoter inducible by human IL-4. As a result of such association, cells stably transformed by a recombinant vector comprising a reporter gene operatively linked to a promoter comprising the $Fc_\epsilon RII$ IL-4 responsive element produce increased levels of the reporter gene product in the presence of human IL-4.

The term "germline ε transcript promoter" is defined herein to mean a part of the 5' region of the human germline ε transcript gene which, when operatively associated with a reporter gene, renders expression of the reporter gene inducible by human IL-4. As a result of such association, cells stably transformed by a recombinant vector comprising a reporter gene operatively linked to a germline ε transcript promoter produce increased levels of the reporter gene product in the presence of human IL-4.

Both the $Fc_\epsilon RII$ IL-4 responsive element and the germline ε transcript promoter are regarded herein as "human IL-4-responsive elements," or simply "responsive elements."

As used herein, human "IL-4" means a protein which (a) has an amino acid sequence substantially identical to the sequence of mature human IL-4 disclosed in FIG. 1C of International Patent Application Publication No. WO 87/02990 and (b) has biological activity that is common to native IL-4. Substantial identity of amino acid sequences means that the sequence of another IL-4 compared to the sequence disclosed by the published patent application is identical or differs by one or more amino acid alterations (deletions, additions, substitutions) that do not substantially impair biological activity.

Figure 6:
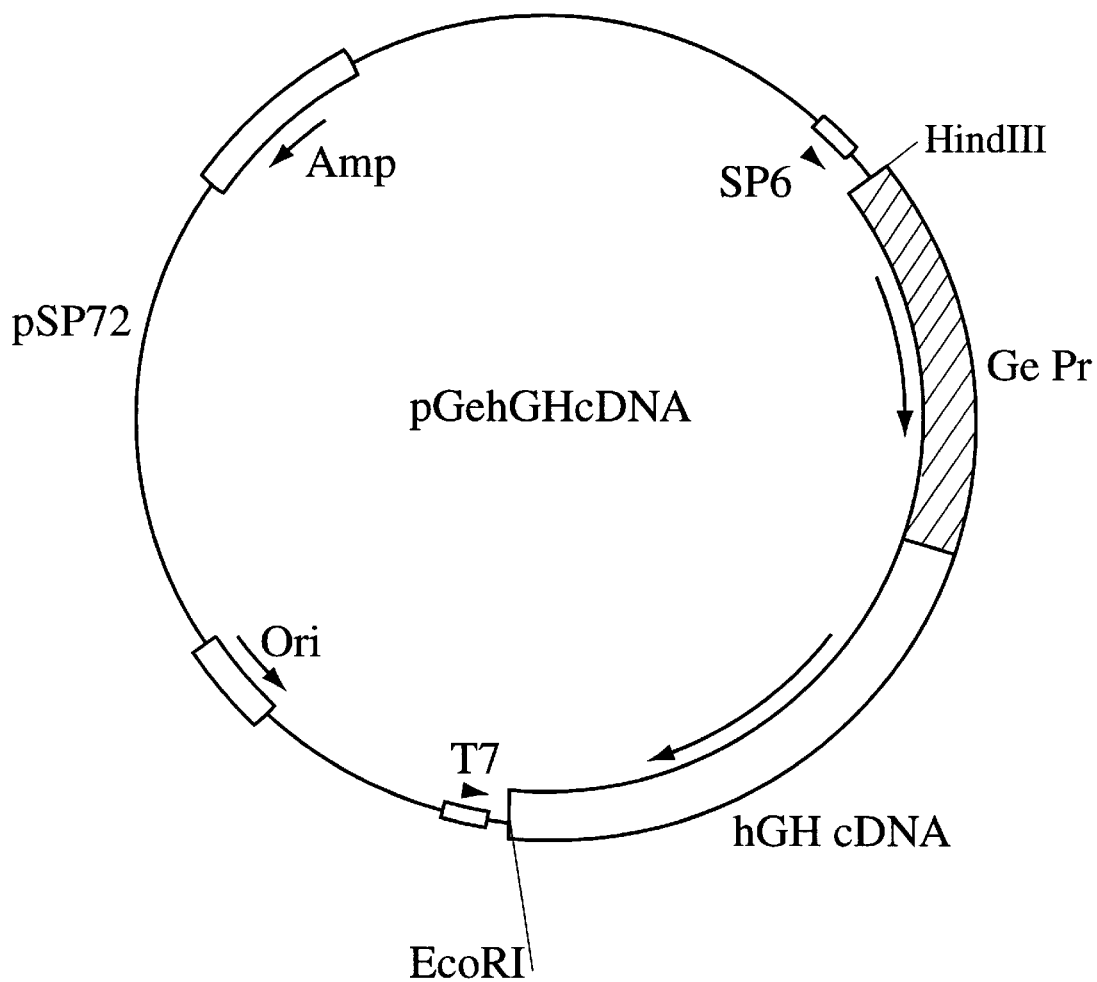
FIG. 6 is a schematic representation of plasmid pGehGHcDNA.

Much of the human $Fc_\epsilon RII$ gene nucleotide sequence is known [see FIG. 6 of Suter et al., Nuc. Acids Res. 15:7295 (1987); Genbank Accession No. X06049]. Relevant portions from the 5'-region of this sequence are defined in the Sequence Listing by SEQ ID NO: 1, wherein the adenine residue at position 551 corresponds to the 5'-most transcription initiation site (+1) of the human $Fc_\epsilon RII$ gene, and residues 1 and 1127 correspond to bases −550 and +577, respectively, of the gene (FIG. 6, Suter et al., supra).

In SEQ ID NO: 1, bases 521–527 and 536–541 are functional TATA motifs, while bases 441–450 form a non-functional TATA-like sequence. Start sites of the mRNA are at positions 551 and 566. A CCAAT and a GC-rich box are at positions 415–419 and 820–830, respectively.

Detailed nucleotide sequence information for the human immunoglobulin switch regions has been published by Mills et al. [Nucleic Acids Res. 18:7305 (1990)]. Relevant portions from this sequence are defined in the Sequence Listing by SEQ ID NO: 2, wherein bases 1–587 correspond to bases 1–587 of the sequence shown in FIG. 4 of Mills et al.

As noted above, some of the responsive elements used in this invention comprise an $Fc_\epsilon RII$ IL-4 responsive element operatively associated with a promoter. Although the promoter used can in principle be the $Fc_\epsilon RII$ gene promoter, in practice the choice of a promoter will be dictated by the host cell selected for transformation. For example, expression of an $Fc_\epsilon RII$ IL-4 responsive element in association with the $Fc_\epsilon RII$ gene promoter was not detectable following stable transformation into Jijoye cells. Expression of such a promoter may, however, be detectable in other cell types.

Results obtained with a particular promoter construct, reporter gene and host cell will be influenced by factors well known in the art such as, e.g., compatibility of the promoter and the reporter gene, and the host cell background. Whether a given promoter is suitable for use in a particular host cell can be determined by routine experimentation.

For use in Jijoye cells it is preferred that the $Fc_\epsilon RII$ IL-4-responsive element be associated with another promoter and/or enhancer element to form a hybrid promoter. For example, a hybrid promoter comprising the DNA segment from position −253 to −44 (bases 298 to 507 of SEQ ID NO: 1) of the $Fc_\epsilon RII$ gene upstream of the thymidine kinase core promoter which has been described by Suter et al., supra, can be used in this invention.

The use of a hybrid promoter is desirable when it increases the signal strength of the reporter gene used, while maintaining inducibility by human IL-4. Because it possesses these properties, a hybrid $Fc_\epsilon RII$ IL-4-responsive element/SV40 early promoter is especially preferred for use in this invention in conjunction with an *E. coli* LacZ reporter gene.

The promoters used in this invention can be prepared by standard methods based upon the known nucleotide sequences of the promoter elements. For example, they can be chemically synthesized using the phosphoramidite solid support method of Matteucci et al. [J. Am. Chem. Soc. 103:3185 (1981)], the method of Yoo et al. [J. Biol. Chem. 764:17078 (1989)], or other well known methods.

Alternatively, since the sequences of the responsive elements and the site specificities of the many available restriction endonucleases are known, one skilled in the art can readily identify and isolate the elements from genomic DNA, vectors or other sources and cleave the DNA to obtain a desired sequence. The polymerase chain reaction (PCR) method [Saiki et al., Science 239:487 (1988)] can also be used to obtain the same result, or to synthesize a complementary strand after the first strand has been prepared by chemical synthesis. Primers used for PCR can also be designed to introduce appropriate new restriction sites, to facilitate incorporation into a given vector.

Any human cell line of myeloid or lymphoid lineage can be used as a source of genomic DNA from which the desired portions of the human Fc$_\epsilon$RII gene or germline $\epsilon$ transcript promoter can be obtained. Human genomic libraries can also be prepared from such cell lines by standard methods if desired.

Of course, there may be allelic variants of the Fc$_\epsilon$RII IL-4 responsive element or germline $\epsilon$ transcript promoter. Furthermore, it is well within the skill of the art, e.g., by chemical synthesis or by the use of modified PCR primers or site-directed mutagenesis to modify the genomic DNA, to prepare various derivatives of the sequences defined by SEQ ID NO: 1 or SEQ ID NO: 2 in which there are single or multiple base substitutions which do not substantially impair the ability of the sequences to respond to IL-4 induction in essentially the same way as the unmodified sequences. Such conservatively modified variants are within the scope of this invention.

The sequence defined by the sequence of bases 7 to 587 in SEQ ID NO: 2 is a germline $\epsilon$ transcript promoter sequence that can be used to confer IL-4 inducibility on operatively-linked reporter genes. Those skilled in the art will appreciate, however, that constructs for use in this invention may also contain fewer bases, and that they can also contain additional flanking bases from the germline $\epsilon$ transcript promoter gene or otherwise.

For example, in one embodiment in the Examples below, a plasmid designated 933-24 served as a source from which a useful germline $\epsilon$ transcript promoter was obtained by PCR. A resulting PCR product had a nucleotide sequence defined by the sequence of bases 7 to 587 of SEQ ID NO: 2, flanked at the 5' and 3' ends by specific restriction sites, to facilitate subsequent cloning. The flanking sequences were defined by the oligonucleotide primers used.

In another embodiment, plasmid 933-24 was instead subjected to restriction endonuclease cleavage using HindIII and BclI. The resulting DNA fragment had a sequence defined by the sequence of bases 1 to 587 of SEQ ID NO: 2, flanked at the 5' end by five bases between the HindIII and BamHI sites that were from plasmid 933-24 but were not part of the germline $\epsilon$ transcript promoter.

Insertion of the promoters and reporter genes into a vector is easily accomplished when the termini of both the DNAs containing such elements and the vector comprise compatible restriction sites. If this is not the case, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

The responsive elements can be inserted into many mammalian reporter gene-containing vectors, including but not limited to plasmids pSV2Apap, pMAMneo-CAT, pMAMneo-LUC, pSVOCAT, pBCO, pBLCAT2, pBLCAT3, pON1, pCH110, pØGH, pIL-4 RE-SV40-LacZ, pSP72 and various plasmids described by De Wet et al., supra. Where a desired vector contains a different promoter, such promoter can be excised using standard methods and replaced by a human IL-4-responsive element. Alternatively, the IL-4-responsive element can be placed in association with another promoter to render it inducible by IL-4.

As used herein, the term "recombinant vector" includes both recombinant plasmids such as those mentioned above and recombinant retroviral vectors, which can also be engineered as described by Geller et al. [Proc. Natl. Acad. Sci. USA 87:1149 (1990)] to contain a promoter operatively linked to a reporter gene.

Any of the well-known reporter genes can be operatively linked to one of the responsive elements. Examples of suitable reporter genes include but are not limited to E. coli LacZ [β-galactosidase; An et al., Mol. Cell. Biol. 2:1628 (1982)], xanthine-guanine phosphoribosyl transferase [Chu et al., Nucleic Acids Res. 13:2921 (1985)], galactokinase [Shumperli et al., Proc. Natl. Acad. Sci. USA 79:257 (1982)], interleukin-2 [Cullen, Cell 46:973 (1986)], thymidine kinase [Searle et al., Mol. Cell. Biol. 5:1480 (1985)], firefly luciferase [De Wet et al., Mol. Cell. Biol. 7:725 (1987)], alkaline phosphatase [Henthorn et al., Proc. Natl. Acad. Sci. USA 85:6342 (1988)], secreted placental alkaline phosphatase [Berger et al., Gene 66:1 (1988)] and chloramphenicol acetyltransferase (CAT) [Gorman et al., Mol. Cell. Biol. 2:1044 (1982); Tsang et al., Proc. Natl. Acad. Sci. USA 85:8598 (1988)].

A preferred reporter gene for use in conjunction with an Fc$_\epsilon$RII/SV40 hybrid promoter used to illustrate the present invention below is the E. coli LacZ gene. The expression level of this gene can be measured by a sensitive fluorescent substrate assay.

For use in Jijoye cells, it is preferred that the germline $\epsilon$ transcript promoter be operatively linked to an E. coli LacZ or a human growth hormone cDNA reporter gene, the use of both of which is exemplified below. The expression level of the LacZ gene can be measured by a sensitive fluorescent substrate assay. Human growth hormone is secreted by human cell lines, thereby eliminating the need to disrupt cells during assay.

Plasmids containing the human growth hormone gene for use as such or as a source of mRNA for the production of human growth hormone cDNA are available commercially, e.g., from Nichols Institute Diagnostics, San Juan Capistrano, Calif. One skilled in the art could instead also isolate the gene by standard methods from a human cell line such as the JAR cell line (ATCC HTB 144), preferably using PCR and primers based upon the known nucleotide sequence of the gene [Denoto et al., Nucleic Acids Res. 9:3719 (1981)].

Expression products of the reporter genes can be measured using standard methods. For example, bioassays can be carried out for biologically active proteins such as interleukin-2. Enzyme assays can be performed when the reporter gene product is an enzyme such as alkaline phosphatase. Alternatively, various types of immunoassays such as competitive immunoassays, direct immunoassays and indirect immunoassays may be used.

Such immunoassays involve the formation of immune complexes containing the reporter gene product and and a measurable label. As used herein, the term "label" includes moieties that can be detected directly, such as fluorochromes and radiolabels, and moieties such as enzymes that must be reacted or derivatized to be detected.

The particular label used will depend upon the type of immunoassay used. Examples of labels that can be used include, e.g., radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as the various luciferin compounds; and enzymes such as horseradish peroxidase, alkaline phosphatase, lysozyme and glucose-6-phosphate dehydrogenase.

The antibody or reporter gene product, as the case may be, can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels.

In competitive immunoassays, samples from induced cultures (following cell disruption if the reporter gene product is not secreted) are incubated with an antibody against the reporter gene product and a known amount of labeled reporter gene product. Any unlabeled product produced by the cells competes with the labeled material for binding to the antibody. The resulting immune complexes are separated and the amount of labeled complex is determined. The reporter gene product produced by the cells can be quantified by comparing observed measurements to results obtained from standard curves.

Direct immunoassays involve incubating culture samples with a labeled antibody against the reporter gene product and separating any immune complexes that form. The amount of label in the complexes is determined and can be quantified by comparison to standard curves.

Enzyme-linked immunosorbant assays (ELISAs) can also be carried out by well known methods, e.g., as described in U.S. Pat. No. 4,665,018 to Vold.

The above-mentioned recombinant vectors can be used to stably transform any human cell line that is capable of responding to human IL-4 by induction of $Fc_\epsilon RII$ or germline ε transcript gene expression. Many such cell lines are available including, e.g., lines of human Burkitt's lymphoma cells such as Jijoye (ATCC CCL 87), BJAB, BL2, BL30, BL49, BL70, Ramos (ATCC CRL 1596), Daudi (ATCC CCL 213) and Namalwa (ATCC CRL 1432) cells; lines of human histiocytic lymphoma cells such as U937 cells (ATCC CRL 1593); and EBV-transformed lymphoblastoid cell lines such as RPMI 8866, IM 9, MO 14, BME and UD 30 cells.

Although cells used in the present invention could in principle be transiently transformed, stably-transformed cells are preferred. Stable transformation of a human cell line can be accomplished by using standard methods to co-transfect the cells with one of the above-mentioned recombinant vectors and with a second vector (such as pSV2neo or pRSVneo) which confers resistance to a selection agent such as an antibiotic. Alternatively, transformation can be carried out with a single vector containing both the promoter/reporter gene construct and the selection marker gene.

In the Example below, co-transfection was carried out using plasmid pRSVneo, one of a number of commercially available plasmids which provide a dominant selectable marker for resistance to antibiotic G418 (neomycin) in mammalian cells.

In screening for IL-4 agonists, cells are provided which are transformed with one of the recombinant vectors of the invention. The cells are plated in a number of culture dishes or in multi-well culture plates in a culture medium appropriate to the kind of cells used and then contacted with samples suspected to contain an IL-4 agonist. These samples can be, e.g., aqueous or water-miscible solutions in which isolated compounds have been dissolved, or individual or pooled fractions from purification steps such as chromatography or preparative electrophoresis. Negative (sample buffer only) and positive (known amounts of IL-4) controls are run in parallel.

After incubation of the cells for an induction period, the level of expression of the reporter gene produced by each sample is measured by an assay appropriate for the gene used. The optimal time for making the measurement is determined by routine experimentation but will typically be in the range of about 24 to 72 hours. An IL-4 agonist in a sample will be identified by measuring a level of reporter gene expression that is higher than the unstimulated (buffer control) level.

Preferably, the level measured in the presence of an IL-4 agonist will be at least about 10% above the unstimulated level. More preferably, the level of induction will be about double, and most preferably, about four or five times the unstimulated level. The strength of an agonist thus identified can be quantified by comparing the level measured with the levels produced by serial dilutions of IL-4 having a known specific biological activity.

In screening for IL-4 antagonists, transformed cells are plated as described above and then contacted with a quantity of IL-4 determined by routine experimentation to produce strong induction of reporter gene expression, with and without samples suspected to contain an IL-4 antagonist. After incubation of the cells for the induction period, the level of expression of the reporter gene is measured for each sample. An IL-4 antagonist in a sample will be identified by measuring a decreased level of reporter gene expression, compared to the level produced by the IL-4 alone.

Preferably, the level measured in the presence of an IL-4 antagonist will be at least about 10% below the level produced by the IL-4 alone. More preferably, the level will be about one-fourth or one-fifth the level produced by IL-4 alone. Most preferably, the level will be essentially that produced by the complete absence of IL-4. Of course, the degree of reduction of reporter gene expression produced by a given antagonist will be determined, e.g., by the strength of the antagonist and the amount of the antagonist in the sample, compared to the quantity of IL-4 used.

As is illustrated in an Example below, the sensitivity of the methods employing the human germline ε transcript promoter can be substantially enhanced by the addition of anti-CD40 antibodies during the screening processes. One such antibody is a monoclonal antibody, designated mAb 89, which has been described by Vallé et al. [Eur. J. Immunol. 19:1463 (1989)]. Polyclonal antibodies and other monoclonal antibodies against CD40 for use in this invention can be prepared by standard methods, although the use of monoclonal antibodies is preferred.

EXAMPLES

The present invention can be illustrated by the following, non-limiting examples. Unless otherwise specified, percentages given below for solids in solid mixtures, liquids in liquids, and solids in liquids are on a wt/wt, vol/vol and wt/vol basis, respectively.

Materials

Restriction endonucleases were purchased from New England Biolabs, Beverly, Mass.; T4 DNA ligase was from International Biotechnologies, Inc., New Haven, Conn.; and *Thermus aquaticus* (Taq) DNA polymerase was obtained from Beckman Inc., Fullerton, Calif. Calf intestine alkaline phosphatase was supplied by Promega Corporation, Madison, Wis. All enzymes were used in accordance with the manufacturers' instructions. The Sequenase version 2.0 sequencing system was obtained from United States Biochemical, Cleveland, Ohio.

Recombinant human IL-4 was prepared in a Chinese hamster ovary (CHO) expression system and purified by standard methods. This IL-4 had a specific biological activity of about $10^7$ units/milligram, with a unit of activity defined as the amount of IL-4 that induces a half-maximal response in a cell proliferation assay [Le et al., J. Biol. Chem. 263:10817 (1988)]. Recombinant IL-4 that is adequate for use in the present invention can also be purchased, e.g., from Genzyme Corporation, Boston, Mass.

A neutralizing murine anti-human-IL-4 monoclonal antibody designated 25D2 was prepared using standard methods. Neutralizing antibodies against human IL-4 are also available commercially, e.g., from Genzyme Corporation.

A 232 bp oligonucleotide having a sequence defined in part in the Sequence Listing by a subsequence of SEQ ID NO: 1 and synthetic oligonucleotide primers having nucleic acid sequences defined in the Sequence Listing by SEQ ID NO: 3 (primer B1348), SEQ ID NO: 4 (primer B1356), SEQ ID NO: 5 (primer B1573), SEQ ID NO: 6 (primer B1574), SEQ ID NO: 7 (primer B2300), SEQ ID NO: 8 (primer B2301), SEQ ID NO: 9 (primer B2379) and SEQ ID NO: 10 (primer B2380) were synthesized by standard methods using an Applied Biosystems Model 380B Synthesizer.

Cell Culture

The human Jijoye cell line (American Type Culture Collection, Rockville, Md.; ATCC CCL 87) used as host and G418-resistant derivative cell lines were grown in RPMI 1640 medium (Hazelton or JRH Biosciences, Lenexa, Kans.) supplemented with 15% horse serum (donor herd, from Sigma, St. Louis, Mo.), 5% heat-inactivated fetal bovine serum (GIBCO/BRL, Rockville, Md.), 2 mM L-glutamine, 50 µg/ml Streptomycin and 100 IU/ml Penicillin (GIBCO/BRL). This medium is referred to as "normal growth medium" below. The antibiotic G418 (GIBCO/BRL) was added to the medium where indicated. Cells were cultured at 37° C. in a humidified atmosphere containing 5% $CO_2$.

Construction of Plasmid pIL-4 RE-SV40-LacZ

Standard recombinant DNA methods were carried out for all of the plasmids described below, essentially as described by Maniatis et al., Molecular Cloning: A Laboratory Manual, 1982, Cold Spring Harbor Laboratory.

A 232-base long oligonucleotide containing the 210 bp IL-4 responsive element from the 5'-flanking region of the $Fc_{\epsilon}RII$ gene (Suter et al., supra) from position −253 to −44 (bases 298 to 507 in the sequence defined by SEQ ID NO: 1) relative to the 5'-most transcription initiation site, flanked at the 5' end by a XhoI restriction site (as shown in SEQ ID NO: 3) and at the 3' end by a HindIII site (as shown in SEQ ID NO: 4), was synthesized using an Applied Biosystem model 380B nucleic acid synthesizer. The double-stranded DNA fragment was obtained by PCR amplification of the synthetic long oligonucleotide using oligonucleotide primers B1348 (SEQ ID NO: 3) and B1356 (SEQ ID NO: 4).

The PCR product was gel-purified, digested with XhoI and HindIII, and then cloned into a pBluescript II KS- plasmid (Stratagene, La Jolla, Calif.). The correct sequence of the full-length IL-4 responsive element was verified by DNA sequencing.

Plasmid pCH110 (Pharmacia LKB Biotechnology Inc., Piscataway, N.J.) containing the SV40 early promoter/enhancer and β-galactosidase (LacZ) was used as the source of the β-galactosidase reporter gene and SV40 early promoter/enhancer. Plasmid pCH110 was digested with HindIII and BamHI, and a resulting 3.85 kb DNA fragment containing the β-galactosidase gene was gel-purified and ligated into plasmid pBluescript II KS-, which had been digested with HindIII and BamHI. The resulting plasmid was designated pLacZ.

The pBluescript II KS- plasmid containing the IL-4 responsive element described above was digested with XhoI and HindIII, and the IL-4 responsive element DNA fragment was gel-purified and subcloned into plasmid pLacZ which had been digested with XhoI and HindIII. The resulting plasmid containing both the IL-4 responsive element and the LacZ gene was designated pIL-4 RE-LacZ.

A DNA fragment containing the SV40 early promoter/enhancer was obtained by PCR using plasmid pCH110 as the DNA template and oligonucleotide primers B1573 (SEQ ID NO: 5) and B1574 (SEQ ID NO: 6). These primers contain incorporated HindIII restriction sites to facilitate cloning into plasmid pIL-4 RE-LacZ.

Figure 1:
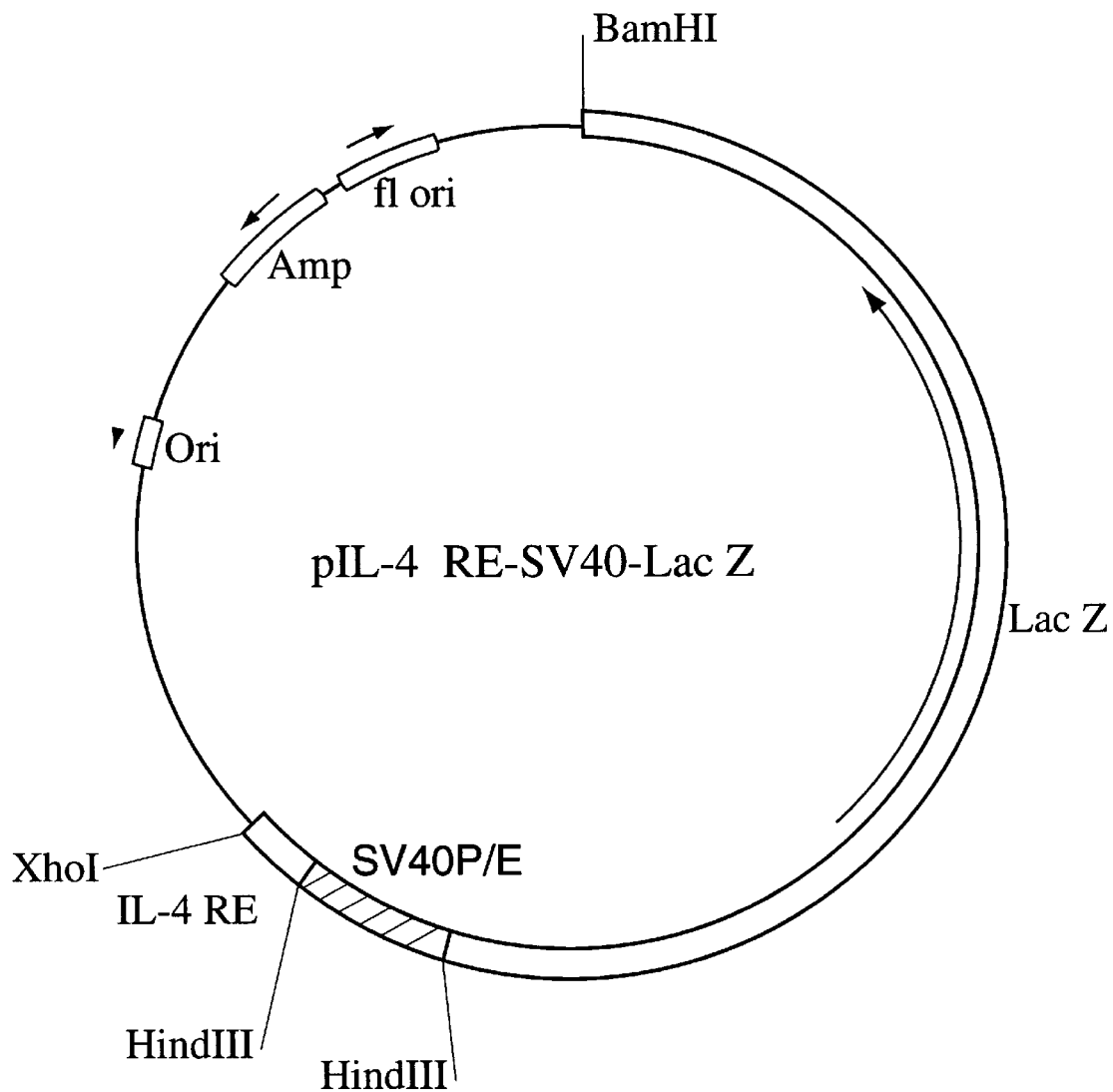
FIG. 1 is a schematic representation of plasmid pIL-4 RE-SV40-LacZ. The CD23 IL-4 responsive element is shown between restriction sites for XhoI and HindIII. The SV40 early promoter/enhancer is shown between two HindIII sites as a hatched box. The β-galactosidase (LacZ) gene shown between HindIII and BamHI restriction sites is from plasmid pCH110, and the plasmid backbone is from pBluescript II KS-.

The 355 bp PCR DNA product was gel-purified and digested with HindIII. Plasmid pIL-4 RE-LacZ was also digested with HindIII and then dephosphorylated by calf intestine alkaline phosphatase, after which the PCR fragment was ligated into the plasmid to produce plasmid pIL-4 RE-SV40-LacZ (FIG. 1).

Construction of Plasmid pGeLacZ

The germline ε transcript promoter was obtained by PCR using plasmid 933-24 (ATCC 75223) as the template and oligonucleotide primers designated B2300 (SEQ ID NO: 7) and B2301 (SEQ ID NO: 8), which incorporate XhoI and HindIII restriction sites, respectively.

Figure 5:
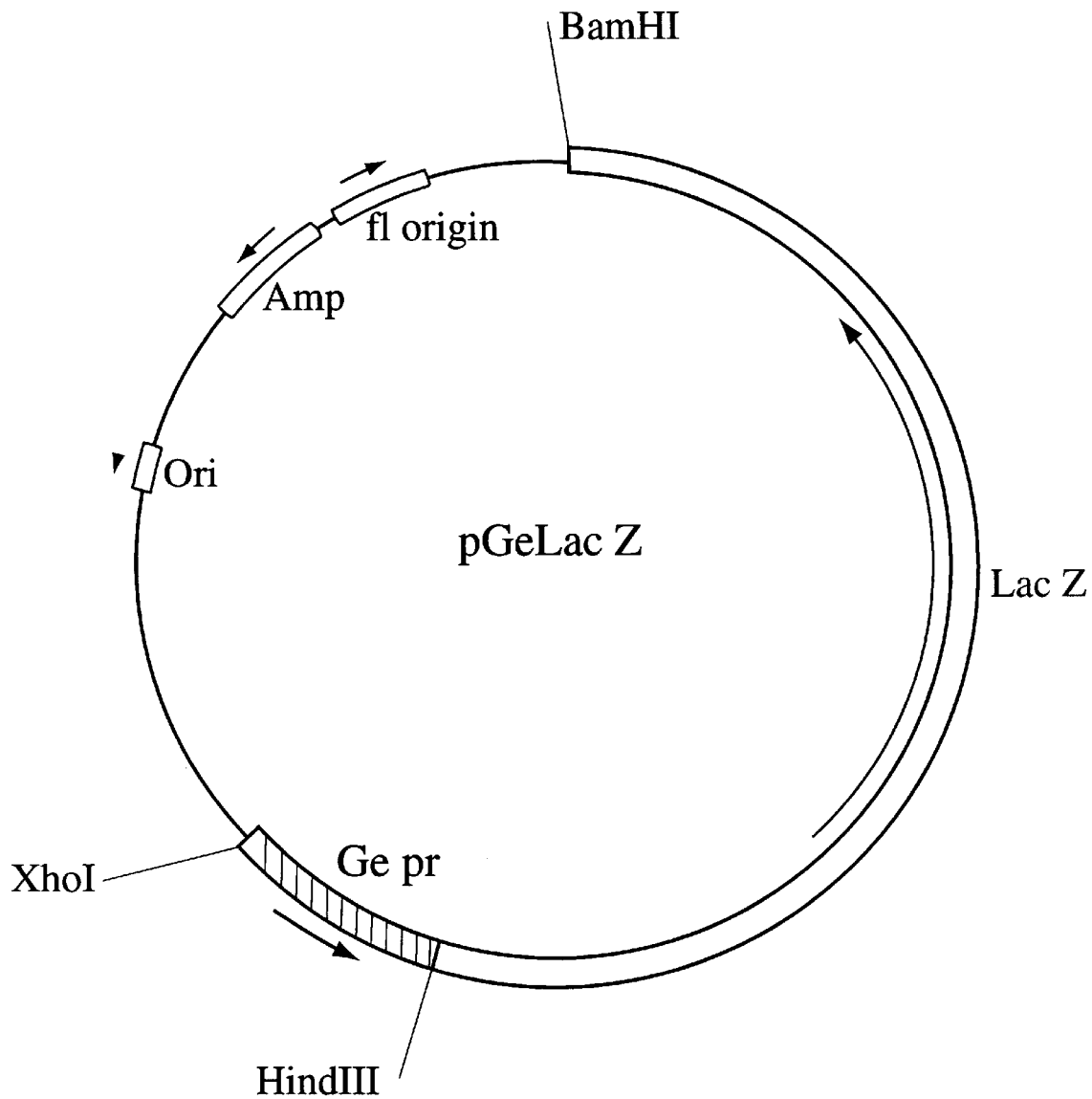
FIG. 5 is a schematic representation of plasmid pGeLacZ.

The 599 bp PCR DNA product was digested with XhoI and HindIII and gel-purified. Plasmid pIL-4 RE-SV40-LacZ was also digested with XhoI and HindIII, to excise the IL-4-responsive element and the SV40 early promoter/enhancer. The digested, purified PCR DNA product was then ligated into the cleaved plasmid, to produce a plasmid designated pGeLacZ, in which the LacZ reporter gene was operatively linked to the germline ε transcript promoter. A restriction map of pGeLacZ is shown in FIG. 5.

Construction of Plasmid pGehGHcDNA

A recombinant plasmid capable of directing expression of the human growth hormone gene was used to stably transform human Jijoye cells (ATCC CCL 87) by co-transfection with plasmid pRSVneo (ATCC 37198), essentially as described below. A clone manifesting high-level, constitutive production of human growth hormone was identified by ELISA and used as a source of poly (A)+ mRNA template for cDNA synthesis and PCR amplification.

The poly (A)+ mRNA produced by the clone was isolated by standard methods, using a commercial mRNA purification kit (QUICKPREP® mRNA Purification Kit, Pharmacia, Piscataway. N.J.) following the manufacturer's instructions.

Briefly, $5 \times 10^7$ human Jijoye cells expressing human growth hormone were pelleted by centrifugation, and 1.5 ml of Extraction Buffer (QUICKPREP® mRNA purification kit, Pharmacia, Piscataway, N.J.) were added to the pelleted cells after removal of the supernatant fluid. The cells were disrupted by vigorous vortex mixing, and 3 ml of Elution Buffer [10 mM Tris-HCl, 1 mM ethylenediaminetetraacetic acid (EDTA),pH 7.4] were added to the extract and mixed thoroughly. The diluted extract was centrifuged at 1000×g for 5 minutes at room temperature.

Four milliliters of the supernatant fluid were transferred to an oligo (dT)-cellulose spun column, gently mixed with the resin by inverting the column, and centrifuged at 350×g for 2 minutes. The supernatant fluid was discarded, and the resin was washed three times with 3 ml of High Salt Buffer (10 mM Tris-HCl, 1 mM EDTA, 0.5 M NaCl, pH 7.4), and then washed twice with 3 ml of Low Salt Buffer (10 mM Tris-HCl, 1 mM EDTA, 0.1 M NaCl, pH 7.4).

The bound poly (A)+ RNA was eluted using four successive washes with 0.25 ml of Elution Buffer pre-warmed to 65° C., after which the eluted mRNA was precipitated by adding 100 $\mu$l of 2.5 M potassium acetate solution, pH 5.0; 20 $\mu$l of 10 mg/ml glycogen in DEPC-treated (diethyl pyrocarbonate-treated) water and 2 ml of 95% ethanol (chilled to −20° C.). The precipitated mRNA was then resuspended in 20 $\mu$l of Elution Buffer.

An aliquot of the mRNA was then subjected to cDNA first-strand synthesis using Molony murine leukemia virus RNaseH− reverse transcriptase (M-MLV H− RT [Superscript], GIBCO/BRL), following the manufacturer's instructions.

Briefly, 4 $\mu$l of the isolated mRNA were mixed with 50 pmole of a 3' end primer (primer B2380; SEQ ID NO: 10), and distilled water was added to a final volume of 12 $\mu$l. The mixture was heated to 70° C. for 10 minutes and then quickly chilled on ice. The contents of the tube were collected by brief centrifugation, and 4 $\mu$l of 5× Reaction Buffer (1× reaction buffer contains 50 mM Tris-HCl, 75 mM KCl, 3 mM MgCl$_2$, pH 8.3), 2 $\mu$l of 0.1 M dithiothreitol (DTT) and 1 $\mu$l of mixed dNTP stock (10 mM each of dATP, dGTP, dCTP and dTTP at neutral pH) were added to the tube. The solution was mixed by gentle vortexing, collected by brief centrifugation, and placed at 37° C. for 2 minutes to equilibrate the solution at that temperature. Finally, 1 $\mu$l (200 units) of M-MLV H− RT was added, mixed gently and incubated at 37° C. for 1 hour.

An aliquot of the reverse transcriptase reaction mixture was then used an the template for PCR, using the 3' end primer B2380 and a specific 5' end primer B2379 (SEQ ID NO: 9), which incorporate EcoRI and BamHI restriction sites, respectively, to facilitate cloning. An 844 bp PCR product containing authentic human growth hormone (hGH) cDNA was digested with BamHI and EcoRI and then gel-purified. After subcloning into cloning vector pSP72 (Promega, Madison, Wis.), the hGH cDNA was verified both by restriction analysis and partial DNA sequencing.

The germline $\epsilon$ transcript promoter was obtained by digesting plasmid 933-24 with HindIII and BclI. An approximately 600 bp DNA fragment containing the promoter was gel-purified and then ligated together with the above-mentioned BamHI/EcoRI hGH cDNA fragment into cloning vector pSP72 which had previously been cleaved with HindIII and EcoRI. The resulting plasmid, containing the human growth hormone cDNA reporter gene operatively linked to the germline $\epsilon$ transcript promoter, was designated pGehGHcDNA. A restriction map of this plasmid is shown in FIG. 6.

Cell Transformation

Human Jijoye cells (ATCC CCL 87) were freshly split 16 to 24 hours before transformation by electroporation and seeded at a density of $5 \times 10^5$ cell/ml. The following day, the cells were collected by centrifugation (1,000 rpm, 3–5 min.), counted and resuspended in normal growth medium at a density of $2 \times 10^7$ cell/ml. Jijoye cells ($5 \times 10^6$) in 250 $\mu$l of the medium were placed into a disposable electrophoretic cuvette (4 mm) and preincubated with 5 $\mu$g of plasmid pIL-4 RE-SV40-LacZ and 0.5 $\mu$g of pRSVneo (ATCC 37198), or with 10 $\mu$g of plasmid pGeLacZ or pGehGHcDNA and 1 $\mu$g of pRSVneo, at room temperature for 10 minutes. The cells were then subjected to a voltage pulse of 200 V at a capacitance of 960 $\mu$F using a Gene Pulser apparatus with capacitance extender (BioRad, Rockville Center, N.Y.).

Following a recovery period of another 10 minutes at room temperature, the Jijoye cells were gently dispersed in 10 ml of normal growth medium in a 25 cm$^2$ flask. Forty-eight hours post-electroporation, the cells were centrifuged as described above and resuspended in 40 or 80 ml of normal growth medium containing 1 mg/ml G418. About 1.2 or $2.5 \times 10^4$ cells per 200 $\mu$l per well were seeded into 96-well plates and placed under G418 selection. The wells containing individual G418-resistant clones were picked and expanded into 24-well plates, and subsequently into 25 cm$^2$ flasks for screening using a β-galactosidase assay or a human growth hormone ELISA assay.

β-Galactosidase Assay

The stably transformed Jijoye cells were assayed for β-galactosidase activity using a modification of the method of Norton et al. [Mol. Cell. Biol. 5:281 (1985)]. This assay employed the fluorescent substrate 4-methylumbelliferyl-β-galactoside (MUG reagent; Sigma Chemical Co., St. Louis, Mo.) as described by Geballe et al. [Cell 46:865 (1986)].

Briefly, after expanding individual G418-resistant stable clones, equal numbers of cells from each stable clone were seeded into 24-well microtiter dishes (about $4.2 \times 10^5$ cells in a total volume of 1.4 ml/well) with different concentrations of the recombinant human IL-4. After 48–72 hours of incubation at 37° C., the cells from each well were transferred into a 1.5 ml Eppendorf tube and sedimented in a microcentrifuge at 10,000 rpm for 1 minute. After removing the supernatant fluid, the cell pellets were suspended in 1 ml of phosphate-buffered saline (PBS) and centrifuged again as described above.

After discarding the supernatant fluid, the cell pellets were resuspended in PBS (100–300 $\mu$l, depending the size of the cell pellet) using a vortex mixer. Equal volumes of 0.2% sodium dodecylsulfate (SDS) in PBS were added to the suspensions to lyse the cells by vigorous vortexing, after which 40 $\mu$l aliquots of the cell lysates were pipetted into the wells of a 96-well Falcon plate. One-hundred-sixty microliter aliquots of Z buffer (60 mM Na$_2$HPO$_4$, 40 mM NaH$_2$PO$_4$, 10 mM KCl, 1 mM MgSO$_4$ and 50 mM β-mercaptoethanol; final pH 7.0) containing 60 $\mu$M freshly prepared MUG reagent were added to each well.

The plate was gently shaken and incubated at 37° C. After a period of incubation (4 hours unless otherwise indicated), the plate was measured on a MICRO-FLUOR® reader (DYNATECH, Chantilly, Va.) and the β-galactosidase activity, expressed in fluorescent signal units as defined by the manufacturer, was determined after subtracting background measurements made in control wells containing MUG reagent but buffer instead of cell lysate.

Human Growth Hormone ELISA Assay

The supernatants of stably transformed Jijoye cells producing human growth hormone were subjected to ELISA analysis using a flat-bottomed Nunc immuno-plate which was prepared as follows. Each well of the plate was coated with 100 µl of sheep anti-hGH (1:2,000, from BIODESIGN International) in 50 mM carbonate/bicarbonate buffer (pH 9.5) one day prior to assay. The plates were sealed and incubated overnight at 4° C.

The plates were then incubated for 90 minutes at room temperature with 250 µl/well of BLOTTO® [5% non-fat dry milk with 0.05% TWEEN 20® (polyoxyethylenesorbitan monolaurate) in Dulbecco's phosphate buffered saline (DPBS)] to saturate protein binding sites. Following the incubation, the plates were washed three times with 150 µl aliquots of Wash Buffer (10 mM potassium phosphate, 0.05% TWEEN 20®, pH 7.4).

After expanding individual G418-resistant stable Jijoye clones producing human growth hormone, equal numbers of cells from each stable clone were seeded into 96-well microtiter dishes (about $1.25 \times 10^5$ cells in a total volume of 250 µl/well) with different concentrations of the recombinant human IL-4. After 72 hours of incubation at 37° C., 100 µl aliquots of the culture media in the wells were transferred to the prepared immuno-plate wells (after removal of the last wash solution), and the plate was incubated for 90 minutes at room temperature.

Following the incubation the plate was washed three times with Wash Buffer as before, after which the last aliquots of wash solution were replaced with 100 µl aliquots of rabbit anti-hGH antiserum (1:1,000) in Assay Buffer [0.25% BSA, 0.05% TWEEN 20® and 1% sheep serum (Sigma) in DPBS] and the plate was incubated for 90 minutes at room temperature. After washing the plate 3 times as before, 100 µl aliquots of peroxidase-conjugated goat anti-rabbit IgG (1:10,000 in Assay Buffer; Boehringer Mannheim) were added to each well, and incubation was continued for 60 minutes at room temperature.

After washing the wells 3 times as before, color reaction was initiated by adding to each well 100 µl of ABTS (2,2'-Azino-di-[3-ethylbenzthiazoline sulfonate] substrate solution (1 mg/ml ABTS in ABTS buffer; Boehringer Mannheim) and incubating the plate for 25 minutes at room temperature. Color development was then measured with an ELISA plate reader at 405 nm.

Characterization of Transformants

Ten stably-transformed clones transfected with plasmid pIL-4 RE-SV40-LacZ were analyzed for β-galactosidase activity after stimulation by recombinant human IL-4 as described above, with the results shown in FIG. 2. The data in FIG. 2 were obtained using (from left to right for each clone) 0, 0.2, 2.0 and 20 ng/ml recombinant human IL-4.

Figure 2:
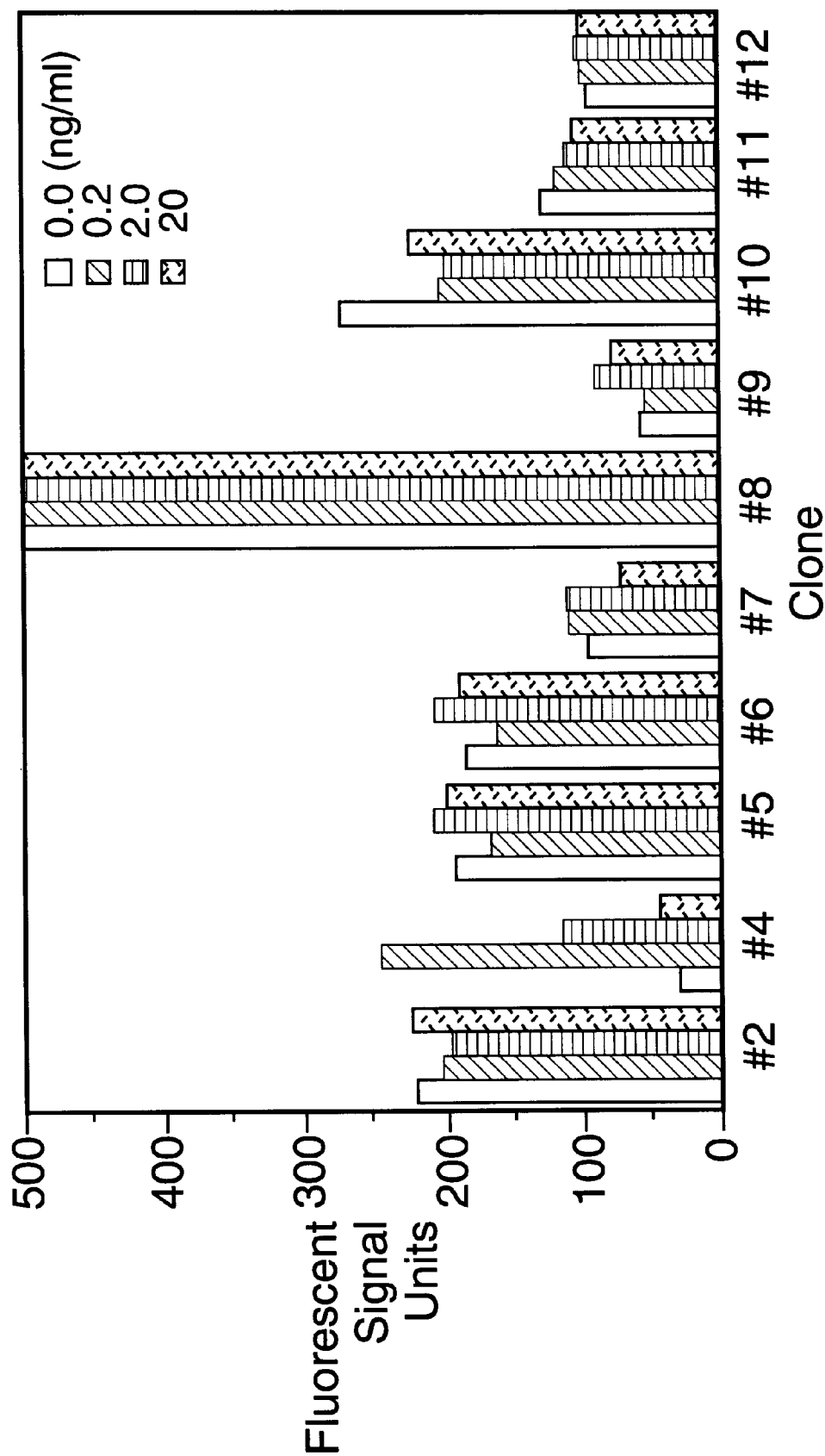
FIG. 2 is a graphical representation of the induction of β-galactosidase (LacZ) activity by human IL-4 in 10 Jijoye clones stably transformed with plasmids pIL-4 RE-SV40-LacZ and pRSVNEO. The clones were cultured in the presence of (from left to right within each set) 0, 0.2, 2.0 and 20 ng/ml recombinant human IL-4. β-Galactosidase activity (Fluorescent Signal Units) in lysates of the cells is shown as a function of IL-4 concentration for each of the clones. The values for clone #8, too high to be shown, were 3878, 3745, 3796 and 3710 Fluorescent Signal Units, from left to right.

As shown in FIG. 2, only clone No. 4 (designated clone J4) responded to the IL-4 by producing increased levels of β-galactosidase activity. All of the other clones showed constitutive expression of the LacZ gene at various levels that was unaffected by IL-4.

To further characterize clone J4, a β-galactosidase assay was carried out on the clone and on untransformed (control) Jijoye cells following stimulation by lower levels of the recombinant IL-4, as described above. The results are shown in FIG. 3, where the data were obtained using (from left to right within each data set) 0, 0.0002, 0.002, 0.02, 0.2 and 2 ng/ml recombinant human IL-4.

Figure 3:
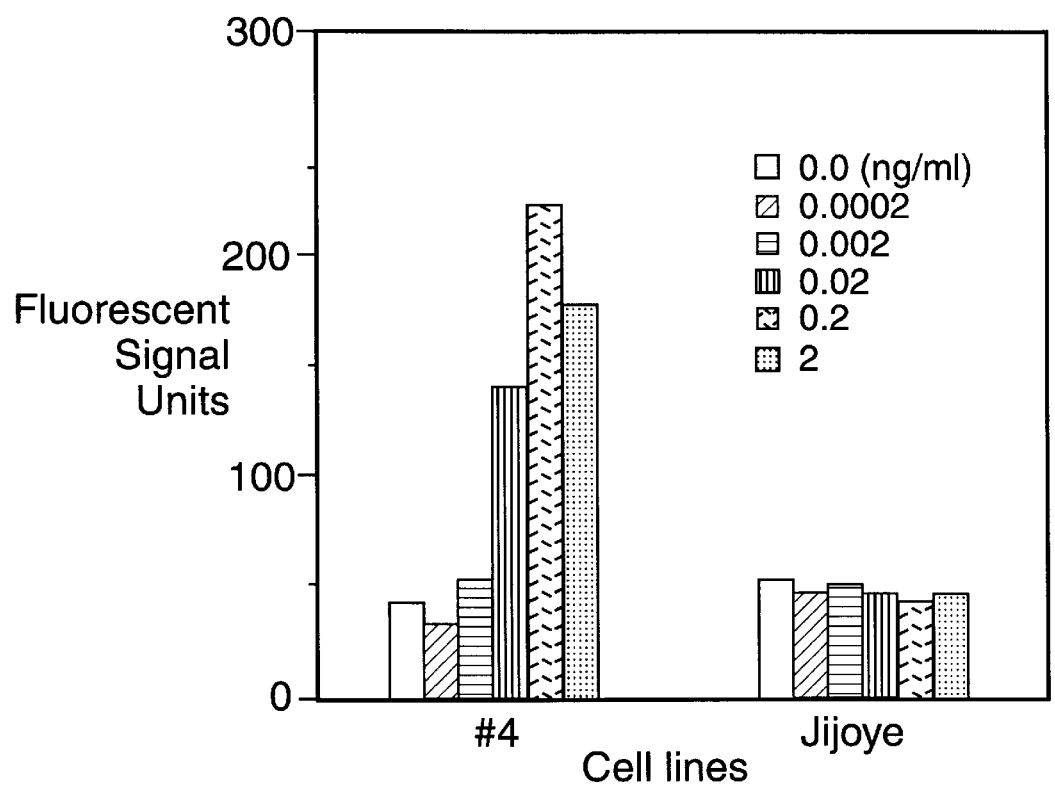
FIG. 3 is a graphical representation of the effects of human IL-4 on the induction of β-galactosidase (LacZ) activity in Jijoye clone No. 4 (FIG. 2) and untransformed Jijoye cells. The cells were cultured in the presence of (from left to right within each set) 0, 0.0002, 0.002, 0.02, 0.2 and 2 ng/ml recombinant human IL-4. β-galactosidase activity (Fluorescent Signal Units) in lysates of the cells is shown as a function of IL-4 concentration.

As shown in FIG. 3, the control cells produced a low level of β-galactosidase activity that was unaffected by the presence of IL-4. In contrast, clone J4 responded to increasing levels of IL-4 with the induction of increasing levels of β-galactosidase activity in a dose-dependent fashion, with a five-fold maximal induction. Optimal induction was observed at an IL-4 concentration of 0.2–2.0 ng/ml. This is comparable to the amount of human IL-4 required for optimal induction of endogenous CD23 in Jijoye cells as determined by fluorescence analysis.

Detection of IL-4 Antagonists

Figure 4:
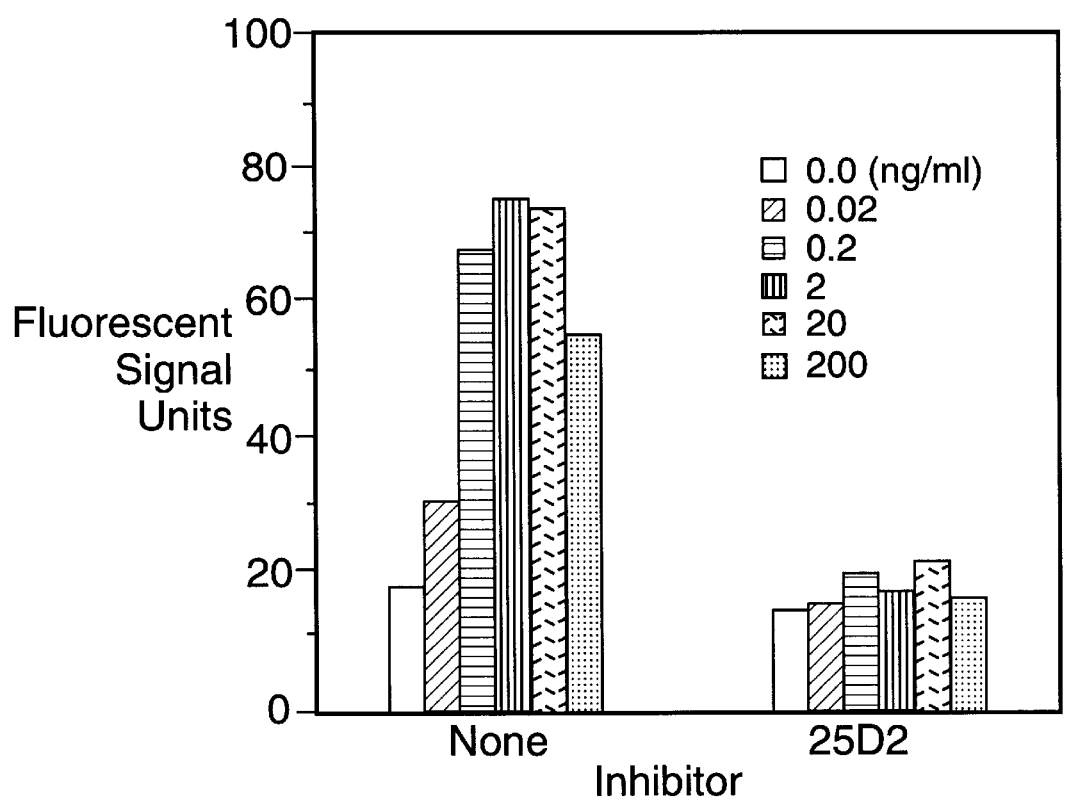
FIG. 4 is a graphical representation of the effects of a neutralizing anti-IL-4 monoclonal antibody on the induction of β-galactosidase synthesis by varying levels of human IL-4 in Jijoye clone No. 4 (FIG. 2). Cell lysate β-galactosidase activity (Fluorescent Signal Units) is shown as a function of IL-4 concentration, both with (25D2) and without (None) the antibody. The cells were cultured in the presence of (from left to right within each set) 0, 0.02, 0.2, 2, 20 and 200 ng/ml recombinant human IL-4.

To demonstrate the effect of an IL-4 antagonist on the induction of β-galactosidase activity in clone J4 by IL-4, cells of the clone were incubated as described above with various quantities of recombinant human IL-4 with and without 175 ng/ml of neutralizing anti-human IL-4 monoclonal antibody 25D2. The results are shown in FIG. 4, where the data were obtained using (from left to right within each set) 0, 0.02, 0.2, 2, 20 and 200 ng/ml recombinant human IL-4. As shown in FIG. 4, antibody 25D2 completely blocked the induction of the β-galactosidase production by human IL-4 in clone J4.

A number of Jijoye clones stably transformed with plasmid pGeLacZ were analyzed for β-galactosidase activity after stimulation by recombinant human IL-4 as described above. One representative clone designated clone 14 was selected for use in a human IL-4 antagonist screen, with the results shown in FIG. 7.

Figure 7:
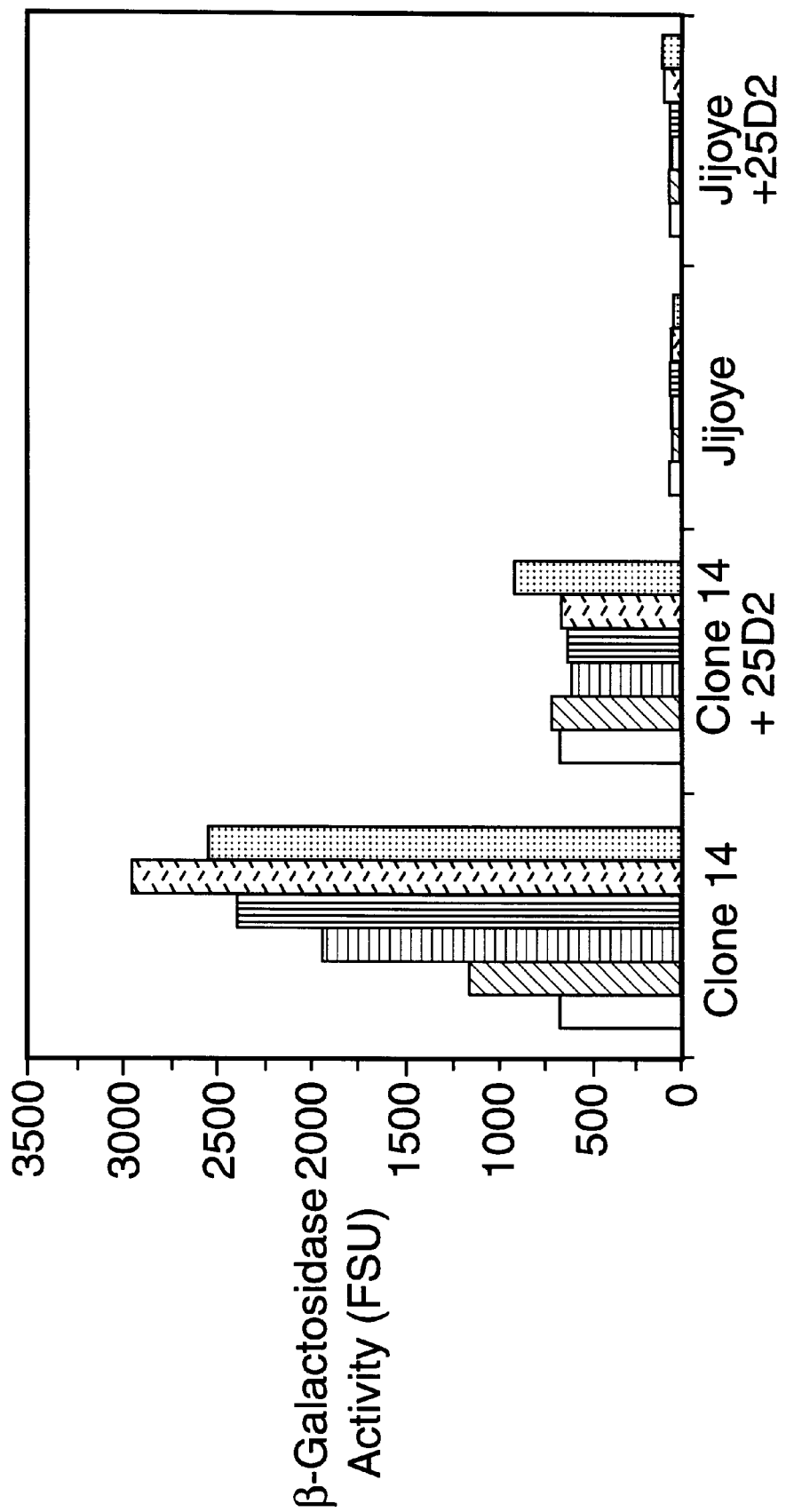
FIG. 7 is a graphical representation of the induction of β-galactosidase activity by human IL-4 in a Jijoye clone (Clone 14) stably transformed with plasmid pGeLacZ, both in the presence and absence of a monoclonal antibody (25D2) against human IL-4. The concentration of IL-4 (from left to right within each data set) was 0, 0.02, 0.2, 2.0, 20 and 200 ng/ml. β-Galactosidase activity in Fluorescent Signal Units (FSU) in lysates of the cells is shown as a function of IL-4 concentration.

The data in FIG. 7 were obtained using (from left to right within each data set) 0, 0.02, 0.2, 2.0, 20 and 200 ng/ml recombinant human IL-4 as described above, with and without 7.5 µl of a concentrated monoclonal antibody 25D2 supernatant containing 35 ng/µl IgG protein. Data were also obtained using untransformed Jijoye cells, with and without the antibody.

As shown in FIG. 7, where the data represent the average of duplicate sample- points following a 1-hour incubation, clone 14 responded to the IL-4 in an essentially concentration-dependent manner, producing increased levels of β-galactosidase activity. In the presence of antibody 25D2, the observed production of β-galactosidase activity was reduced to the background (uninduced) level. As expected, induction by IL-4 of β-galactosidase activity was not observed in the untransformed Jijoye cells, whether the antibody was present or not.

A number of Jijoye clones stably transformed with plasmid pGehGHcDNA were analyzed by ELISA for growth hormone production following stimulation by recombinant human IL-4 as described above. Two representative clones designated clones 5 and 12 were selected for use in a human IL-4 antagonist screen, with the results shown in FIG. 8.

Figure 8:
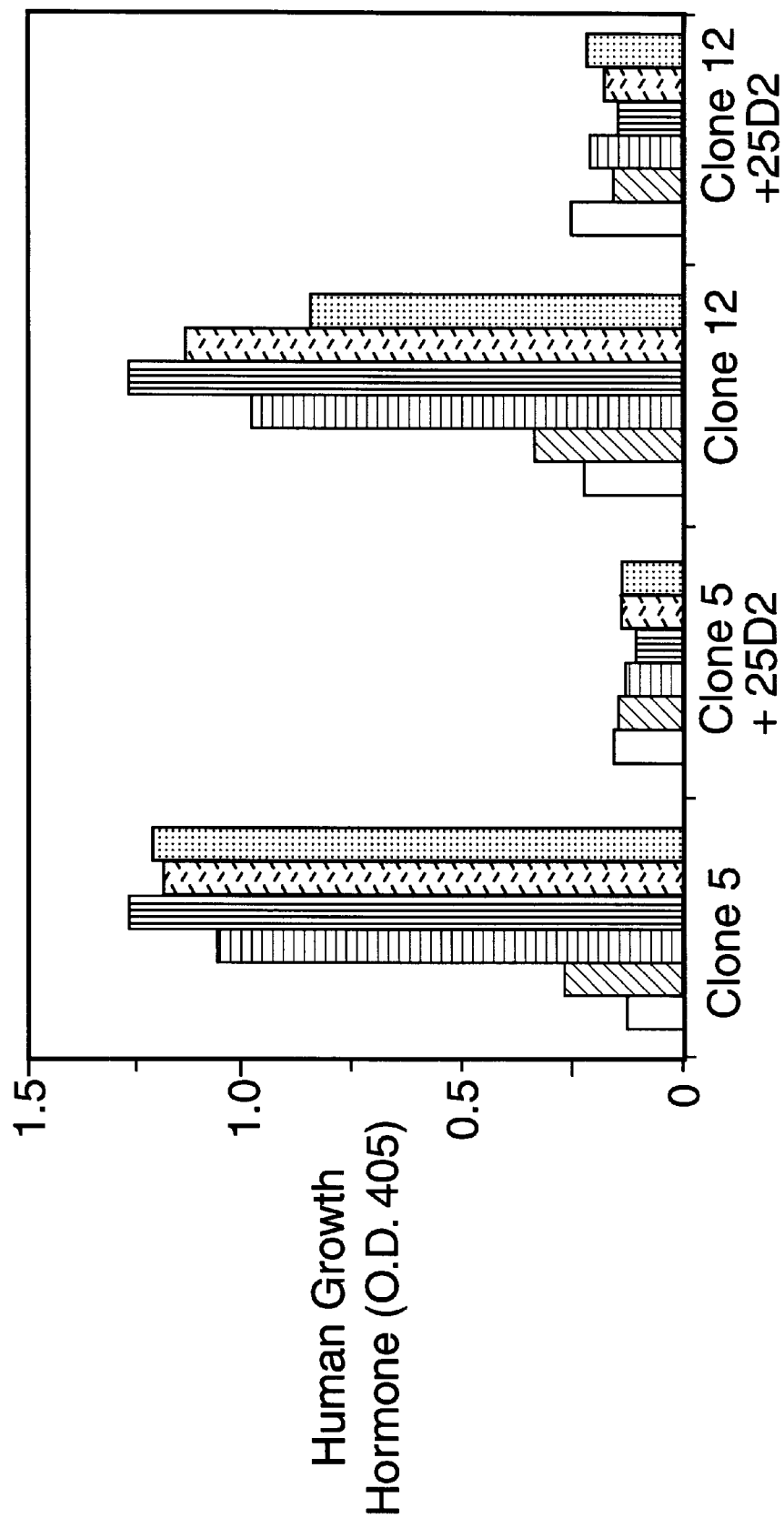
FIG. 8 is a graphical representation of the induction of human growth hormone synthesis by human IL-4 in two Jijoye clones (Clone 5 and Clone 12) stably transformed with plasmid pGehGHcDNA, both in the presence and absence of a monoclonal antibody (25D2) against human IL-4. The concentration of IL-4 (from left to right within each data set) was 0, 0.02,0.2, 2.0, 20 and 200 ng/ml. Human growth hormone synthesis as determined by ELISA (O.D. 405 nm) is shown as a function of IL-4 concentration.

The data in FIG. 8 were obtained using (from left to right within each data set) 0, 0.02, 0.2, 2, 20 and 200 ng/ml recombinant human IL-4 as described above, with and without 2.5 µl of the concentrated monoclonal antibody 25D2 supernatant containing 35 ng/µl IgG protein.

As shown in FIG. 8, both clones responded to increasing IL-4 concentrations by producing increased levels of human growth hormone. In the presense of antibody 25D2, the observed production of growth hormone was reduced to the background level.

Enhancement by Anti-CD40 Antibodies

To demonstrate the effect of an anti-CD40 antibody on the sensitivity of methods employing a human germline ε transcript promoter, Jijoye clone 14 cells stably transformed with plasmid pGeLacZ were induced using 20 ng/ml recombinant IL-4 as described above, both in the presence and absence of mAb 89 (Vallé, supra) at a concentration of 1 μg/ml. After incubation for 48 hours, β-galactosidase activity was measured, with the results shown in FIG. 9.

Figure 9:
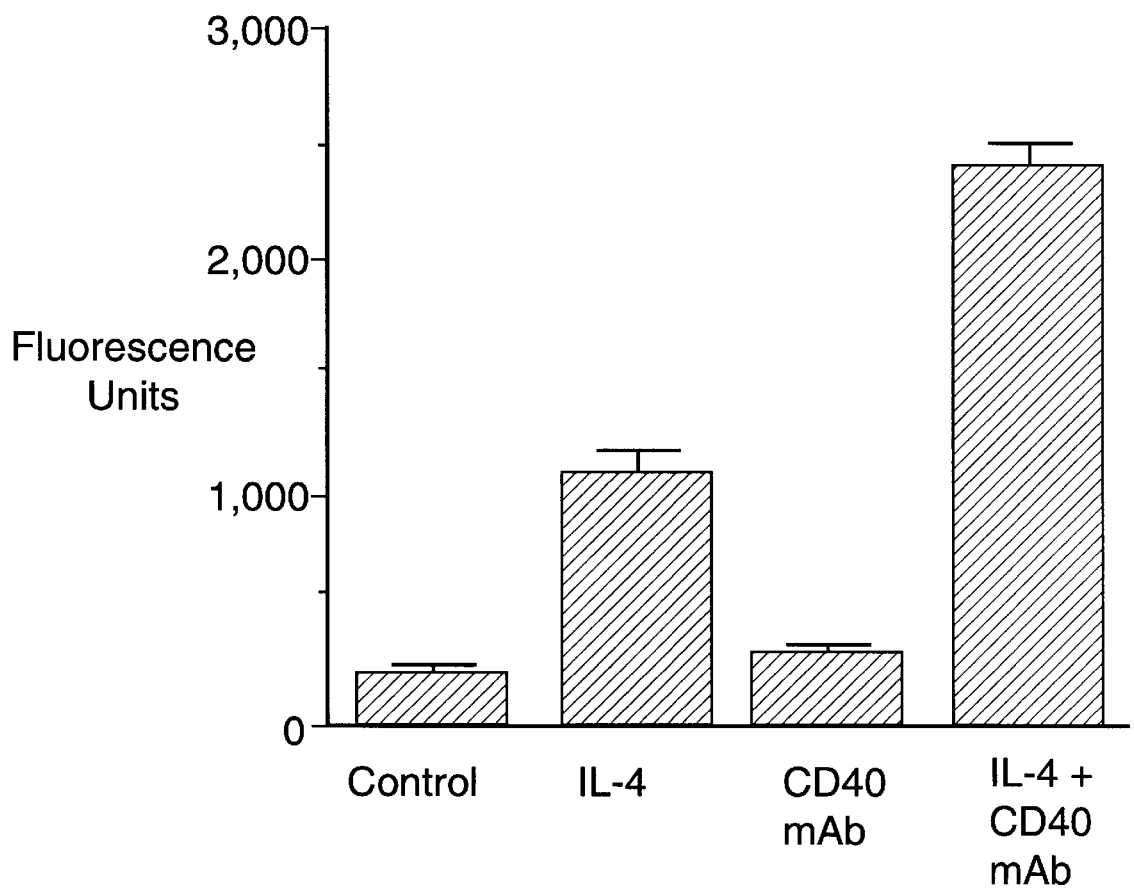
FIG. 9 is a graphical representation of the induction after 48 hours of β-galactosidase (Lac Z) activity by human IL-4 (20 ng/ml) in Jijoye clone 14 stably transformed with plasmid pGeLacZ, both in the presence or absence of an anti-CD40 monoclonal antibody (1 µg/ml). β-Galactosidase activity in lysates of the cells is expressed in Fluorescent Signal Units.

As is evident from FIG. 9, the presence of mAb 89 (CD40 mAb) in the incubation mixture produced a marked increase in the induction of β-galactosidase activity (Fluorescence Units) by IL-4. The antibody alone, however, produced a low level of activity that was comparable to that of the control.

This enhancement by the antibody was further demonstrated during a human IL-4 antagonist screening assay carried out as described above, in which a human IL-4 mutant protein designated hIL-4Y124D was used as the antagonist. This mutant protein, in which the tyrosine residue at position 124 was replaced by an aspartic acid residue by standard procedures as described by Kruse et al. [EMBO J. 11:3237 (1991)] and Zurawski et al. [EMBO J., in press], binds with high affinity to the IL-4 receptor but fails to activate the receptor. Therefore this protein, functions as a potent antagonist of IL-4.

The assay was carried out using the Jijoye clone 14 cells described above and 5 ng/ml IL-4, with or without 1 μg/ml mAb 89 and/or 500 ng/ml mutant protein hIL-4Y124D. Incubation was carried out for 48 hours, after which β-galactosidase activity was measured as described above.

Figure 10:
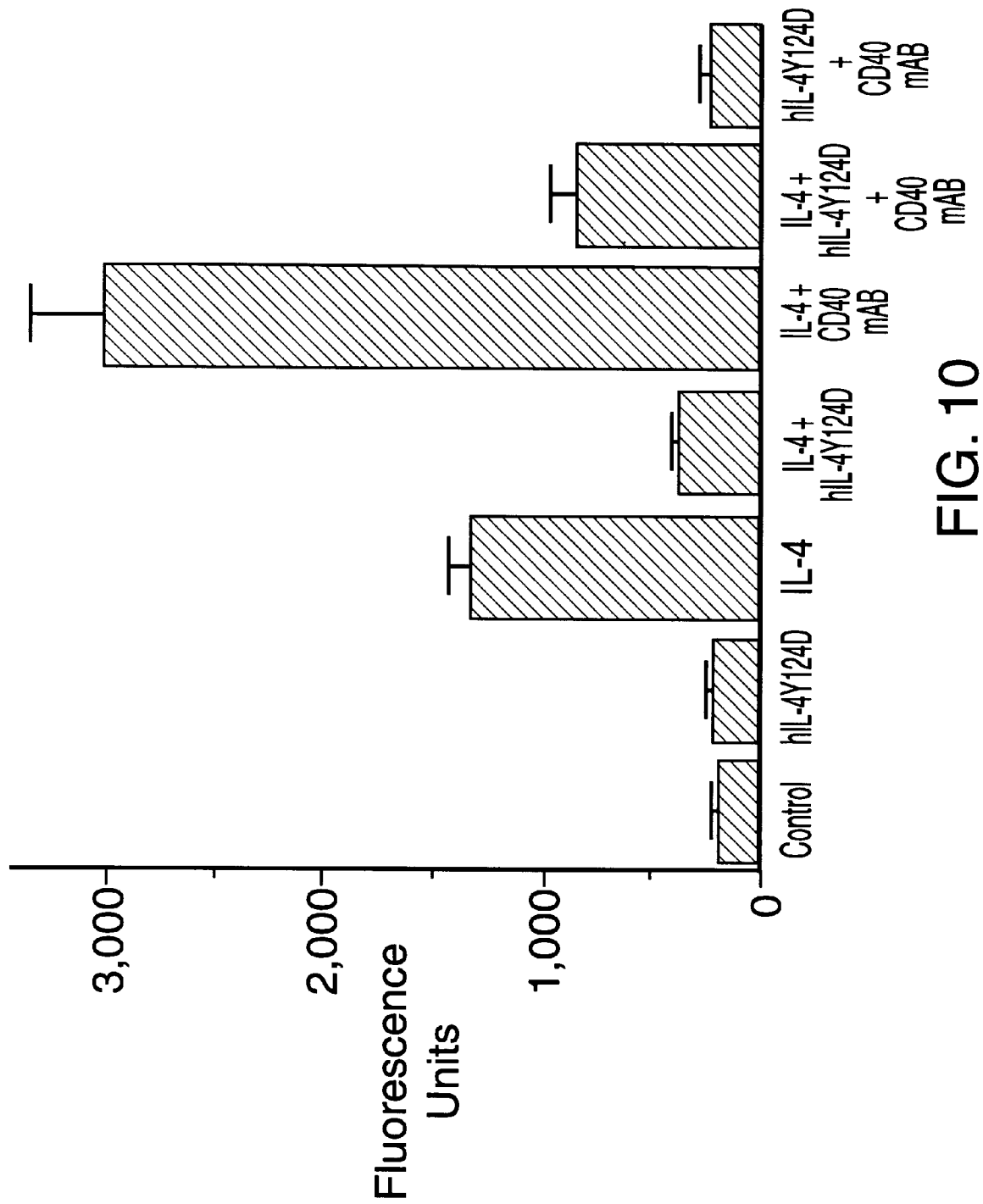
FIG. 10 is a graphical representation of the induction after 48 hours of β-galactosidase (Lac Z) activity by human IL-4 (5 ng/ml) in Jijoye clone 14 stably transformed with plasmid pGeLacZ, both in the presence or absence of an anti-CD40 monoclonal antibody (1 µg/ml) or an IL-4 antagonist, designated hIL-4Y124D (500 ng/ml). β-Galactosidase activity in lysates of the cells is expressed in Fluorescent Signal Units.

The results are shown in FIG. 10, where it can be seen that the combination of IL-4 and mAb 89 (CD40 mAb) again produced a much higher level of β-galactosidase activity (Fluorescence Units) than did IL-4 alone. It can also be seen that the mutant protein hIL-4Y124D alone was completely inactive, and that the activity produced by IL-4 was almost completely abolished in the presence of the mutant protein.

This observation shows that this screening system can be used to detect not only antibody antagonists of IL-4, but antagonists that act at the receptor level as well. Therefore, this screening system has broad utility.

Deposits

Cells from Jijoye clone No. 4 stably transformed with plasmid pIL-4 RE-SV40-LacZ were deposited Sep. 19, 1991 with the American Type Culture Collection (ATCC), Rockville, Md., and assigned Accession No. ATCC CRL 10873. Plasmid 933-24 was deposited Mar. 24, 1992 with the ATCC and assigned Accession No. ATCC 75223. Both deposits were made under the provisions of the Budapest Treaty on the International Recognition of the Deposit of Microorganisms for the Purposes of Patent Procedures.

Many modifications and variations of this invention can be made without departing from its spirit and scope, as will become apparent to those skilled in the art. The specific embodiments described herein are offered by way of example only, and the invention is to be limited only by the terms of the appended claims.

---

What is claimed is:

1. A method for identifying a compound in a sample as a human IL-4 agonist comprising:

(a) providing a cell line expressing receptors for human IL-4, which cell line has been stably transfected by a recombinant vector comprising a reporter gene operatively linked to a human $Fc_\epsilon RII$ IL-4 responsive element comprising nucleotides 298–507 of SEQ ID NO: 1, or to a germline $\epsilon$ transcript promoter comprising nucleotides 7–587 of SEQ ID NO: 2, which responsive element or promoter is capable of controlling expression of the reporter gene in response to IL-4;

(b) contacting the transfected cell line with a sample suspected to contain a human IL-4 agonist, under conditions in which human IL-4 would cause increased expression of the reporter gene; and (c) measuring the level of expression of the reporter gene, whereby a human IL-4 agonist in the sample is identified by measurement of an increased level of expression of the reporter gene, compared to the level produced by a buffer control.

2. The method of claim 1 in which the responsive element has a nucleotide sequence defined by a subsequence of the sequence of SEQ ID NO: 1, which subsequence is delimited at the 5' end by one of bases 1 to 298 and at the 3' end by one of bases 507 to 678 of the sequence defined by SEQ ID NO: 1.

3. The method of claim 2 in which the responsive element has a nucleotide sequence defined by the sequence of bases 298 to 507 of SEQ ID NO: 1.

4. The method of claim 1 in which the cell line is a Jijoye cell line.

5. The method of claim 4 in which the reporter gene is an *E. coli* LacZ gene or a human growth hormone cDNA.

6. The method of claim 4 in which the human $Fc_\epsilon RII$ IL-4-responsive element is operatively associated with an SV40 early promoter.

7. The method of claim 4 in which the cell line has been transformed by plasmid pIL-4 RE-SV40-LacZ, pGeLacZ or pGehGHcDNA.

8. The method of claim 1 in which the responsive element is a human germline $\epsilon$ transcript promoter and the sample of step (b) further contains anti-CD40 antibodies.

9. The method of claim 1 in which the responsive element has a nucleotide sequence defined by (a) the sequence of SEQ ID NO: 1, or by (b) the sequence of SEQ ID NO: 2.

10. A method for identifying a compound in a sample as a human IL-4 antagonist comprising:

(a) providing a cell line expressing receptors for human IL-4, which cell line has been stably transfected by a recombinant vector comprising a reporter gene operatively linked to a human $Fc_\epsilon RII$ IL-4 responsive element comprising nucleotides 298–507 of SEQ ID NO: 1, or to a germline $\epsilon$ transcript promoter comprising nucleotides 7–587 of SEQ ID NO: 2, which responsive element or promoter is capable of controlling expression of the reporter gene in response to IL-4;

(b) contacting the transfected cell line with a sample suspected to contain a human IL-4 antagonist, to which has been added an amount of human IL-4 that, absent such antagonist, would produce a measurable increase in expression of the reporter gene; and (c) measuring the level of expression of the reporter gene, whereby a human IL-4 antagonist in the sample is identified by measurement of a decreased level of expression of the reporter gene, compared to the level produced by the human IL-4 in the absence of such antagonist.

11. The method of claim 10 in which the responsive element has a nucleotide sequence defined by a subsequence of the sequence of SEQ ID NO: 1, which subsequence is delimited at the 5' end by one of bases 1 to 298 and at the 3' end by one of bases 507 to 678 of the sequence defined by SEQ ID NO: 1.

12. The method of claim 11 in which the responsive element has a nucleotide sequence defined by the sequence of bases 298 to 507 of SEQ ID NO: 1.

13. The method of claim 10 in which the cell line is a Jijoye cell line.

14. The method of claim 13 in which the reporter gene is an *E. coli* LacZ gene or a human growth hormone cDNA.

15. The method of claim 13 in which the human $Fc_\epsilon RII$ IL-4-responsive element is operatively associated with an SV40 early promoter.

16. The method of claim 13 in which the cell line has been transfected by plasmid pIL-4 RE-SV40-LacZ, pGeLacZ or pGehGHcDNA.

17. The method of claim 10 in which the responsive element is a human germline $\epsilon$ transcript promoter and the sample of step (b) further contains anti-CD40 antibodies.

18. The method of claim 10 in which the responsive element has a nucleotide sequence defined by (a) the sequence of SEQ ID NO: 1, or by (b) the sequence of SEQ ID NO: 2.

* * * * *